(12) United States Patent
Horn et al.

(10) Patent No.: US 11,220,674 B2
(45) Date of Patent: Jan. 11, 2022

(54) STABILIZATION OF DEHYDROGENASES WITH STABLE COENZYMES

(71) Applicant: ROCHE DIABETES CARE, INC., Indianapolis, IN (US)

(72) Inventors: Carina Horn, Biblis (DE); Dieter Heindl, Paehl (DE); Claudia Gaessler-Dietsche, Schriesheim (DE); Joachim Hoenes, Zwingenberg (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 56 days.

(21) Appl. No.: 15/868,055

(22) Filed: Jan. 11, 2018

(65) Prior Publication Data

US 2018/0265849 A1    Sep. 20, 2018

Related U.S. Application Data

(60) Division of application No. 12/859,654, filed on Aug. 19, 2010, now Pat. No. 9,896,666, which is a continuation of application No. PCT/EP2009/001206, filed on Feb. 19, 2009.

(51) Int. Cl.
*C12N 9/96* (2006.01)
*C12N 9/04* (2006.01)

(52) U.S. Cl.
CPC ............. *C12N 9/0006* (2013.01); *C12N 9/96* (2013.01)

(58) Field of Classification Search
CPC combination set(s) only.
See application file for complete search history.

(56) References Cited

U.S. PATENT DOCUMENTS

| | | | |
|---|---|---|---|
| 5,801,006 A | 9/1998 | Kaufman | |
| 7,341,830 B2 | 3/2008 | Horn et al. | |
| 7,553,615 B2 | 6/2009 | Heindl et al. | |
| 8,809,013 B2 * | 8/2014 | Heindl | C12Q 1/32 435/26 |
| 9,359,634 B2 | 6/2016 | Horn et al. | |
| 2004/0023330 A1 | 2/2004 | Sode | |
| 2005/0214891 A1 | 9/2005 | Horn et al. | |
| 2006/0094099 A1 | 5/2006 | Shao | |
| 2007/0026476 A1 | 2/2007 | Heindl et al. | |

FOREIGN PATENT DOCUMENTS

| | | | |
|---|---|---|---|
| WO | 98/33936 | 8/1998 | |
| WO | 01/49247 | 7/2001 | |
| WO | WO-0149247 A2 * | 7/2001 | ............... C12Q 1/61 |
| WO | 01/94370 | 12/2001 | |
| WO | 2005/045016 | 5/2005 | |
| WO | 2007/012494 | 2/2007 | |
| WO | 2009/103540 | 8/2009 | |
| WO | 2010/009432 | 1/2010 | |

OTHER PUBLICATIONS

Slama, J. et al., Biochemistry 1989 vol. 28, pp. 7688-7694.*
Jiao Ruishen et al., "Introduction of Bioengineering", Chemical Industry Press, Apr. 30, 1991, p. 184.
Okada et al., "Thermostable Mutant Glucose Dehydrogenase Having Stable Quarterly Structure", Protein Engineering, vol. 3, No. 4, p. 303, Mar. 1990.
Biak et al., Cooperative Effect of Two Surface Amino Acid Mutations (Q252L and E170K) in Glucose Dehydrogenase from Bacillus megaterium IWG3 on Stabilization of Its Oligometric State; Jun. 2005, Applied and Environmental Microbiology, vol. 71, No. 6, p. 3285-3293, XP002580338, ISSN: 0099-2240.
Vazquez-Figueroa et al., Development of a Thermostable Glucose Dehydrogenase by a Structure-Guided Consensus Concept; ChemBioChem 2007, 8, p. 2295-2301, InterScience.
International Search Report dated May 6, 2009 of PCT Application No. PCT/EP2009/001206.
Van Den Huevel, et al., "Coenzyme Binding during Catalysis Is Beneficial for the Stability of 4-Hydroxyacetophenoene Monooxygenase", Journal of Biological Chemistry, vol. 280, No. 37, p. 32115-32121, (Sep. 16, 2005).
Pan, et al., "Coenzyme Stabilization of Rat Liver Cystathionine Synthetase and Cystathionase", Journal of the Chinese Biochemical Society, vol. 3, No. 1, pp. 1-8, (1974).
Bertoldi, et al., "Folding pathway of the pyridoxal 5'-phosphate C-S lyase MalY from *Escherichia coli*", Biochem. J. 389, pp. 885-898, (2005).
Tramper, et al., "Progress in Biotechnology 8, Biocatalysis in Non-Conventional Media", Proceedings of an International Symposium Noordwijkerhout, pp. 739-745, (Apr. 26-29, 1992).
"Does Coenzyme Binding Determine Enzyme Stability", Nutrition Reviews, vol. 36, No. 8, pp. 251-524, (Aug. 1978).
Liao, et al., "Characteristics of magnetic nanoparticles-bound YADH in water/AOT/isooctane microemulsions", Journal of Molecular Catalysis B: Enzymatic, 18, pp. 81-87, (2002). XP-002502967.
Slama, et al., "Inhibition of NAO Glycohydrolase and ADP-ribosyl Transferases by Carbocyclic Analogues of Oxidized Nicotinamide Adenine Dinucleotide", Biochemistry, 28, pp. 7688-7694, (1989).
Everse, et al., "The Pyridine Nucleotide Coenzymes", Academic Press New York, London, Chapter 3, pp. 56-65, (1982).
Everse, et al., "The Pyridine Nucleotide Coenzymes", Academic Press New York, London, Chapter 4, (1982).
Kaplan, et al., "Chemistry and Properties of the 3-Acetylpyridine Analogue of Diphosphopyridine Nucleotide", J_ Biol. Chem., 221, pp. 823-832, (Dec. 5, 1955).
Slama, et al., "Carbanicotinamide Adenine Dinucleotide: Synthesis and Enzymological Properties of a Carbocyclic analogue of Oxidized Nicotinamide Adenine Dinucleotide", Biochemistry, 27, pp. 183-193, (1988).

(Continued)

*Primary Examiner* — Heidi Reese
(74) *Attorney, Agent, or Firm* — Quarles & Brady LLP

(57) ABSTRACT

The present invention relates to a method for stabilizing an enzyme by storing the enzyme in the presence of a stable coenzyme. The present invention further relates to an enzyme stabilized with a stable coenzyme, and to the use thereof in test elements for detecting analytes.

20 Claims, 28 Drawing Sheets

Specification includes a Sequence Listing.

(56) References Cited

OTHER PUBLICATIONS

Hutchinson, et al., "Synthesis of carbocyclic NAO+ containing a methylenebisphosphonate linkage for the investigation of ADP-ribosyl cyclase", Chem. Comm., pp. 2765-2766, (1996).
Nagao, et al., "Stability-increasing mutants of glucose dehydrogenase", FEBS Letters, vol. 253, No. 1,2, pp. 113-116 (Aug. 1989).

* cited by examiner

Figure 21

GlucDH_E96G_E170K

MYPDLKGKVVAITGAASGLGKAMAIRFGKE
QAKVVINYYSNKQDPNEMKKDVKKIHFVNMLAEVAPKKV
VVQGDVTKEDVHEMPLKKDIKKVINTLADPKAASYV
NNAGLGSREAIKYAASKGIKNAAVAWLAGRG
FLGSREAIKYFVENDIKRAEIAVSFQAG
PWPLFVHYAASKGINTPIEEIAVYPSFQA
IRVNNIGPGAIHPEEIAVTLYPSFQAGRG
SMIPMGYIGEPEEIAVMTKYPSFQAGRG
GITLFADGGMTLYPSFQAGRG

GlucDH_E170K_K252L

MYPDLKGKVVAITGAASGLGKAMAIRFGKE
QAKVVINYYSNKEDVHEMPLKKDVKKIHFVNMLAEVAPKKV
VVQGDVTKEDVHEMPLKKDIKKVINTLADPKAASYV
NNAGLENPVPSHEVENDIKKFIAVAWLAGRG
FLGSREAIKYFVENDIKRAEIAVSFQAG
PWPLFVHYAASKGINTPIEEIAVYPSFQA
IRVNNIGPGAIHPEEIAVTLYPSFQAGRG
YIGEPEEIAVMTLYPSFQAGRG
GITLFADGGMTLYPSFQAGRG

STABILIZATION OF DEHYDROGENASES WITH STABLE COENZYMES

CLAIM OF PRIORITY

This application is a divisional of U.S. patent application Ser. No. 12/859,654, filed Aug. 19, 2010, which claims benefit to PCT/EP2009/001206 filed Feb. 19, 2009, which claims priority to European Application 08003054.7, filed Feb. 19, 2008, each of which are hereby incorporated by reference in their respective entireties.

TECHNICAL FIELD OF THE INVENTION

The present invention relates to a method for stabilizing an enzyme by storing the enzyme in the presence of a stable coenzyme. The present invention further relates to an enzyme stabilized with a stable coenzyme, and to the use thereof in test elements for detecting analytes.

SEQUENCE LISTING

The instant application contains a Sequence Listing which has been submitted in ASCII format via EFS-Web and is hereby incorporated by reference in its entirety. Said ASCII copy, created on Oct. 28, 2010, is named 24711USD.txt and is 5,472 bytes in size.

BACKGROUND

Biochemical measurement systems are important constituents of clinically relevant methods of analysis. The priority here is to measure analytes, e.g. metabolites or substrates, which are determined directly or indirectly with the aid of an enzyme. The analytes are in this case converted with the aid of an enzyme-coenzyme complex and then quantified. This entails the analyte to be determined being brought into contact with a suitable enzyme and a coenzyme, with the enzyme usually being employed in catalytic amounts. The coenzyme is changed, e.g. oxidized or reduced, by the enzymatic reaction. This process can be detected directly, or electrochemically or photometrically through a mediator. A calibration provides a direct relationship between the measurement and the concentration of the analyte to be determined.

Coenzymes are organic molecules which are bound covalently or non-covalently to an enzyme and which are changed by the conversion of the analyte. Prominent examples of coenzymes are nicotinamide adenine dinucleotide (NAD) and nicotinamide adenine dinucleotide phosphate (NADP), respectively, from which NADH and NADPH, respectively, are produced by reduction.

Measurement systems known in the prior art are notable for being stable for a limited period and for the specific requirements on the environment, such as cooling or dry storage, for achieving this stability. For particular applications, e.g. tests carried out by the final user himself, such as, for example, in the self-monitoring of blood glucose, it is therefore possible for incorrect results to occur through incorrect, unnoticed faulty storage. The exhaustion of desiccants through the primary packaging being opened for too long in particular may lead to faulty measurements which, with some systems, can scarcely be identified by the user.

One known measure employed to increase the stability of biochemical measurement systems is the use of stable enzymes, e.g. the use of enzymes from thermophilic organisms. A further possibility is to stabilize enzymes by chemical modification, e.g. crosslinking, or by mutagenesis. In addition, enzyme stabilizers such as, for example, trehalose, polyvinylpyrrolidone and serum albumin can also be added, or the enzymes can be enclosed e.g. by photopolymerization in polymer networks.

Attempts have also been made to improve the stability of biochemical measurement systems by using stable mediators. Thus, the specificity of tests is increased, and interference during the reaction is eliminated, through the use of mediators with a redox potential which is as low as possible. However, the redox potentials of the enzyme/coenzyme complexes form a lower limit for the redox potential of mediators. Below these potentials, the reaction with the mediators is slowed down or even stopped.

An alternative possibility is also to use biochemical measurement systems without mediators, in which for example there is direct detection of coenzymes, e.g. of the coenzyme NADH. One disadvantage of such measurement systems is, however, that coenzymes such as NAD and NADP are unstable.

NAD and NADP are base-labile molecules whose degradation pathways are described in the literature (N. J. Oppenheimer in The Pyridine Nucleotide Coenzymes, Academic Press New York, London 1982, editors J. Everese, B. Anderson, K. You, Chapter 3, pages 56-65). The degradation of NAD and NADP, respectively, essentially results in ADP-ribose through cleavage of the glycosyl linkages between the ribose and the pyridine unit. The reduced forms NADH and NADPH are on the other hand acid-labile: e.g. epimerization is one known degradation pathway. In both cases, the instability of NAD/NADP and NADH/NADPH derives from the lability of the glycosyl linkage between the ribose unit and the pyridine unit. However, even under conditions which are not drastic, such as, for example, in aqueous solution, the coenzymes NAD and NADP, respectively, are hydrolysed solely through the ambient moisture. This instability may lead to inaccuracies in the measurement of analytes.

A number of NAD/NADP derivatives is described for example in B. M. Anderson in The Pyridine Nucleotide Coenzymes, Academic Press New York, London 1982, editors J. Everese, B. Anderson, K. You, Chapter 4. Most of these derivatives are, however, not well accepted by enzymes. The only derivative which has to date therefore been used for diagnostic tests is 3 acetylpyridine adenine dinucleotide (acetyl NAD) which was described for the first time in 1956 (N. O. Kaplan, J. Biol. Chem. (1956), 221, 823). Also this coenzyme shows a poor acceptance by enzymes and a change in the redox potential.

WO 01/94370 describes the use of further NAD derivatives with a modified pyridine group. Modifications of the nicotinamide group have, however, in general a direct influence on the catalytic reaction. In most cases, this influence is negative.

In a further idea for stabilization, the ribose unit has been altered in order thereby to influence the stability of the glycosyl linkage. This procedure does not directly interfere with the catalytic reaction of the nicotinamide group. However, there may be an indirect influence as soon as the enzyme exhibits a strong and specific binding to the ribose unit. Kaufmann et al. disclose in this connection in WO 98/33936 and U.S. Pat. No. 5,801,006, and in WO 01/49247, respectively, a number of thioribose-NAD derivatives. A connection between the modification of the nicotinamide-ribose unit and the activity of the derivatives in enzymatic reactions has, however, not been shown to date.

CarbaNAD, a derivative without a glycosyl linkage, was described for the first time in 1988 (J. T. Slama, Biochemistry 1989, 27, 183 and Biochemistry 1989, 28, 7688). The ribose therein is replaced by a carbocyclic sugar unit. Although carbaNAD was described as a substrate of dehydrogenases, its activity has not to date been demonstrated clinically in biochemical detection methods.

A similar approach was described later by G. M. Blackburn, Chem. Comm., 1996, 2765, in order to prepare carbaNAD with a methylenebisphosphonate compound instead of the natural pyrophosphate. The methylenebisphosphonate shows increased stability towards phosphatases and was used as inhibitor of ADP-ribosyl cyclase. An increase in hydrolysis stability was not the aim (J. T. Slama, G. M. Blackburn).

WO 2007/012494 and U.S. Ser. No. 11/460,366 disclose stable NAD/NADH and NADP/NADPH derivatives, respectively, enzyme complexes of these derivatives and the use thereof in biochemical detection methods and reagent kits.

An object of the present invention is to provide methods for stabilizing enzymes, especially for the long-term stabilization of enzymes.

SUMMARY

This object and others that will be appreciated by those of ordinary skill in the art are achieved by a method for stabilizing an enzyme, where the enzyme is stored in the presence of a stable coenzyme. It has surprisingly been found that long-term stabilization of several weeks or months at high relative moisture or even in liquid phase and at elevated temperatures is possible with the aid of a stable coenzyme. This perception is surprising because it is known that although enzymes have an increased short-term stability for some hours in the presence of native coenzyme (Bertoldi et al., Biochem. J. 389, (2005), 885-898; van den Heuvel et al., (J. Biol. Chem. 280 (2005), 32115-32121; and Pan et al., (J. Chin. Biochem. Soc. Vol. 3 (1974), pp. 1-8), they have shown a lower stability over a longer period (Nutrition Reviews 36 (1978), 251-254).

Compared with these perceptions in relation to the prior art, it was surprising that an enzyme has a distinctly increased long-term stability in the presence of a stable coenzyme than does an enzyme in the presence of a native coenzyme, especially since the stable coenzymes have a lower binding constant with the enzyme than does the native coenzyme.

The enzyme stabilized by the method of the invention is a coenzyme-dependent enzyme. Examples of suitable enzymes are dehydrogenases selected from a glucose dehydrogenase (E.C. 1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase or amino-acid dehydrogenase, e.g. L-amino-acid dehydrogenase (E.C.1.4.1.5). Further suitable enzymes are oxidases such as, for instance, glucose oxidase (E.C.1.1.3.4) or cholesterol oxidase (E.C.1.1.3.6) and amino transferases, respectively, such as, for example, aspartate or alanine amino transferase, nucleotidase or creatine kinase. The enzyme in certain embodiments is glucose dehydrogenase.

In certain other embodiments of the invention, a mutated glucose dehydrogenase is employed. The term "mutant" as used in the context of the present application refers to a genetically modified variant of a native enzyme which, while the number of amino acids is the same, has an amino acid sequence which is modified compared with the wild-type enzyme, i.e. differs in at least one amino acid from the wild-type enzyme. The introduction of the mutation(s) can take place site-specifically or non-site-specifically, preferably site-specifically by using recombinant methods known in the art, whereas, appropriate for the particular requirements and conditions, at least one amino acid exchange within the amino acid sequence of the native enzyme results. The mutant in yet other embodiments has an increased thermal or hydrolytic stability compared with the wild-type enzyme.

The mutated glucose dehydrogenase can in principle comprise the amino acid(s) which is (are) modified by comparison with the corresponding wild-type glucose dehydrogenase at any position in its amino acid sequence. The mutated glucose dehydrogenase in certain embodiments includes a mutation at at least one of positions 96, 170 and 252 of the amino acid sequence of the wild-type glucose dehydrogenase, with exemplary embodiments comprising mutants with mutations at position 96 and position 170, and mutations at position 170 and position 252. It has proved advantageous for these particular embodiments for the mutated glucose dehydrogenase to comprise no further mutations besides these mutations.

The mutation at positions 96, 170 and 252 can in principle include any amino acid exchange which leads to a stabilization, e.g. an increase in the thermal or hydrolytic stability, of the wild-type enzyme. The mutation at position 96 may include includes an amino acid exchange of glutamic acid for glycine, whereas in relation to position 170 an amino acid exchange of glutamic acid for arginine or lysine, in particular an amino acid exchange of glutamic acid for lysine, is possible. In relation to the mutation at position 252, this typically includes an amino acid exchange of lysine for leucine.

The mutated glycose dehydrogenase can be obtained by mutation of a wild-type glucose dehydrogenase derived from any biological source, where the term "biological source" includes in the context of this invention both prokaryotes such as, for example, bacteria, and eukaryotes such as, for example, mammals and other animals. The wild-type glucose dehydrogenase may be derived from a bacterium, such as glucose dehydrogenase from *Bacillus megaterium*, *Bacillus subtilis* or *Bacillus thuringiensis*.

In one embodiment of the present invention, the mutated glucose dehydrogenase is a glucose dehydrogenase obtained by mutation of wild-type glucose dehydrogenase from *Bacillus subtilis*, which has the amino acid sequence depicted in SEQ ID No.: 1 (GlucDH_E96G_E170K) or that depicted in SEQ ID No.: 2 (GlucDH_E170K_K252L).

The stable coenzyme is a coenzyme which has been chemically modified by comparison with the native coenzyme and which has a higher stability than the native coenzyme (e.g. hydrolytic stability). The stable coenzyme is generally stable to hydrolysis under test conditions. Compared with the native coenzyme, the stable coenzyme may have a reduced binding constant for the enzyme, for example a binding constant reduced by a factor of 2 or more.

Examples of stable coenzymes are stable derivatives of nicotinamide adenine dinucleotide (NAD/NADH) or nicotinamide adenine dinucleotide phosphate (NADP/NADPH), or truncated NAD derivatives, e.g. without the AMP moiety or with non-nucleoside residues, e.g. hydrophobic residues. Likewise another example of stable coenzyme in the context of the present invention is the compound of the formula (I)

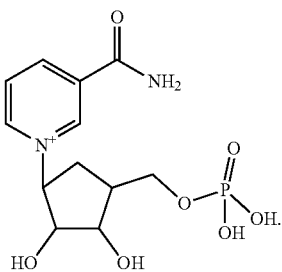

(I)

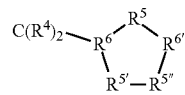

(III)

where a single or double bond may be present between $R^{5'}$ and $R^{5'''}$ with $R^4$=in each case independently H, F, Cl, $CH_3$, $R^5CR_2^4$ where $R^{5'}$=O, S, NH, $NC_1$—$C_2$-alkyl, $CR_2^4$, CHOH, $CHOCH_3$, and $R^{5'''}$=$CR_2^4$, CHOH, $CHOCH_3$ if there is a single bond between $R^{5'}$ and $R^{5'''}$, and where $R^{5'}$=and $R^{5'''}$=$CR^4$ if there is a double bond between $R^{5'}$ and $R^{5'''}$, and $R^6$, $R^{6'}$=in each case independently CH or $CCH_3$.

In one embodiment, the compounds of the invention comprise adenine or adenine analogues such as, for example, $C_8$- and $N_6$-substituted adenine, deaza variants such as 7-deaza, aza variants such as 8-aza or combinations such as 7-deaza or 8-aza or carbocyclic analogues such as formycin, whereas the 7-deaza variants may be substituted in position 7 by halogen, $C_1$-$C_6$-alkynyl, -alkenyl or -alkyl.

In a further embodiment, the compounds comprise adenosine analogues which, instead of ribose, comprise for example 2-methoxydeoxyribose, 2'-fluorodeoxyribose, hexitol, altritol and polycyclic analogues, respectively, such as bicyclo-, LNA- and tricyclo-sugars.

It is possible in particular in the compounds of the formula (II) also for (di)phosphate oxygens to be replaced isotronically, such as, for example, O by S and $BH_3$, respectively, O by NH, $NCH_3$ and $CH_2$, respectively, and =O by =S.

In one embodiment, W in the compounds of the formula (II) of the invention comprises $CONH_2$ or $COCH_3$.

In another embodiment, $R^5$ in the groups of the formula (III) comprises $CH_2$. In yet a further embodiment, $R^{5'}$ is selected from $CH_2$, CHOH and NH. In yet other embodiments, $R^{5'}$ and $R^{5'''}$ each comprise CHOH. In yet a further embodiment, $R^{5'}$ is NH and $R^{5'''}$ is $CH_2$. Specific examples of stabilized coenzymes are depicted in FIGS. 1A and B.

In a typical embodiment, the stable coenzyme is carbaNAD.

Exemplary stable derivatives of NAD/NADH and NADP/NADPH are described in the aforementioned references, the disclosures of each of which are hereby expressly incorporated by reference herein in their respective entireties. Particular stabilized coenzymes are described in WO 2007/012494 and U.S. Ser. No. 11/460,366, respectively, the disclosures of which are hereby expressly incorporated by reference herein in their entireties. The stable coenzyme in one embodiment is selected from compounds having the general formula (II)

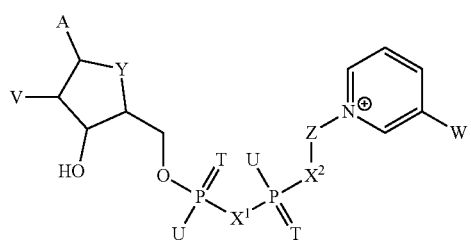

(II)

with

A=adenine or an analogue thereof,

T=in each case independently 0, S,

U=in each case independently OH, SH, $BH_3$, $BCNH_2$,

V=in each case independently OH or a phosphate group, or two groups forming a cyclic phosphate group;

W=COOR, $CON(R)_2$, COR, $CSN(R)_2$ with R=in each case independently H or $C_1$-$C_2$-alkyl, $X^1$, $X^2$=in each case independently O, $CH_2$, $CHCH_3$, $C(CH_3)_2$, NH, $NCH_3$,

Y=NH, S, O, $CH_2$,

Z=a linear or cyclic organic radical, with the proviso that Z and the pyridine residue are not linked by a glycosidic linkage, or a salt or, where appropriate, a reduced form thereof.

In one embodiment, Z in the compounds of the formula (II) comprises a linear radical having 4-6 C atoms, for example 4 C atoms, in which 1 or 2 C atoms are optionally replaced by one or more heteroatoms selected from O, S and N. In other embodiments, Z comprises a radical including a cyclic group which has 5 or 6 C atoms and which optionally comprises a heteroatom selected from), S and N and optionally one or more substituents, and a radical $CR_2^4$, where $CR_2^4$ is bonded to the cyclic group and to $X^2$, with $R^4$=in each case independently H, F, Cl, $CH_3$.

In yet other embodiments, Z comprises a saturated or unsaturated carbocyclic or heterocyclic 5-membered ring, in particular a compound of the general formula (III)

The method of the invention is generally suitable for long-term stabilization of enzymes. This means that the enzyme stabilized with a stable coenzyme shows when stored, e.g. as dry substance, for example over a period of at least 2 weeks, but generally at least 4 weeks and in many cases at least 8 weeks. Furthermore, such stabilization generally results in a decline in enzyme activity of less than 50%, typically less than 30% and in many cases less than 20% in relation to the initial enzyme activity.

The method of the invention further includes a storage of the enzyme stabilized with a stable coenzyme at elevated temperatures, for example at a temperature of at least 20° c., typically at least 25° C., and in many cases at least 30° C. The enzyme activity in this case declines by less than 50%, typically less than 30% and in many cases less than 20% in relation to its initial level.

It is possible by the stabilization according to the invention to store the enzyme stabilized with a stable coenzyme even without a drying reagent for a long time, as indicated above, and/or at high temperatures, as indicated above. It is further possible for the stabilized enzyme also to be stored at a high relative humidity, e.g. a relative humidity of at least 50%, in which case the enzyme activity declines by less than 50%, typically less than 30% and in many cases less than 20% in relation to the initial level.

The storage of the enzyme stabilized with a stable coenzyme can take place on the one hand as dry substance and on the other hand in liquid phase. The storage of the stabilized enzyme in one embodiment takes place on or in a test element suitable for determining an analyte. The enzyme stabilized with a stable coenzyme is in this case typically a constituent of a detection reagent which may where appropriate also comprise further constituents such as, for example, salts, buffers; etc. In some embodiments, the detection reagent is generally free of a mediator.

The enzyme stabilized with a stable coenzyme can be employed for detecting analytes, for example parameters in body fluids such as, for instance, blood, serum, plasma or urine, and in sewage samples or food products, respectively.

Analytes which can be determined are any biological or chemical substances which can be detected by a redox reaction, e.g. substances which are substrates of a coenzyme-dependent enzyme or are themselves coenzyme-dependent enzymes. Examples of analytes are glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LOH), carbon dioxide etc. The analyte in one particular embodiment is glucose.

Another embodiment of the present invention relates to the use of a compound of the invention or of an enzyme stabilized with a stable coenzyme according to the invention for detecting an analyte in a sample by an enzymatic reaction. The detection of glucose with the aid of glucose dehydrogenase (GlucDH) is a typical example in this regard.

The alteration in the stable coenzyme by reaction with the analyte can in principle be detected in any way. It is possible in principle to employ here all methods known from prior art for detecting enzymatic reactions. However, the alteration in the coenzyme in one embodiment is detected by optical methods. Optical detection methods include for example the measurement of absorption, fluorescence, circular dichroism (CD), optical rotatory dispersion (ORD), refractometry etc.

An optical detection method which may be used in the context of the present application is photometry. Photometric measurement of an alteration in the coenzyme as a result of reaction with the analyte requires, however, the additional presence of at least one mediator which increases the reactivity of the reduced coenzyme and makes it possible for electrons to be transferred to a suitable optical indicator or an optical indicator system.

Mediators suitable for the purposes of the present invention are inter alia nitrosoanilines such as, for example, [(4-nitrosophenyl)imino]dimethanol hydrochloride, quinones such as, for example, phenanthrenequinones, phenanthrolinequinones or benzo[h]quinolinequinones, phenazines such as, for example, 1-(3-carboxypropoxy)-5-ethylphenazinium trifluoromethanesulfonate, or/and diaphorase (EC 1.6.99.2). Preferred examples of phenanthrolinequinones include 1,10-phenanthroline-5,6-quinones, 1,7-phenanthroline-5,6-quinones, 4,7-phenanthroline-5,6-quinones, and the N-alkylated and N,N'-dialkylated salts thereof, with preference as counter ion in the case of N-alkylated and N,N'-dialkylated salts, respectively, for halides, trifluoromethanesulfonate or other anions which increase the solubility.

It is possible to use as optical indicator or as optical indicator system any substance which is reducible and on reduction experiences a detectable change in its optical properties such as, for example, colour, fluorescence, reflectance, transmission, polarization or/and refractive index. Determination of the presence or/and the amount of the analyte in the sample can take place with the unaided eye or/and by means of a detection device using a photometric method which appears to be suitable to a person skilled in the art.

Heteropolyacids and in particular 2,18-phosphomolybdic acid are optionally used as optical indicators and are reduced to the corresponding heteropoly blue.

The alteration in the coenzyme in other embodiments is detected by measuring the fluorescence. Fluorescence measurement is highly sensitive and makes it possible to detect even low concentrations of the analyte in miniaturized systems.

An alternative possibility is also to detect the alteration in the coenzyme electrochemically using a suitable test element such as, for example, an electrochemical test strip. The precondition for this is once again the use of suitable mediators which can be converted by the reduced coenzyme, by transfer of electrons, into a reduced form. The analyte is determined by measuring the current which is needed to reoxidize the reduced mediator and which correlates with the concentration of the analyte in the sample. Examples of mediators which can be used for electrochemical measurements include in particular the aforementioned mediators employed for photometric measurements.

It is possible to use a liquid test to detect an analyte, in which case the reagent is for example in the form of a solution or suspension in an aqueous or nonaqueous liquid or as powder or lyophilisate. However, it is also possible to use a dry test, in which case the reagent is applied to a support, a test strip. The support may include for example a test strip including an absorbent or/and swellable material which is wetted by the sample liquid to be investigated.

In one particular embodiment, a test format includes the use of the enzyme glucose dehydrogenase with a stable NAD derivative for detecting glucose, in which case a derivative of the reduced coenzyme NADH is formed. NADH is detected by optical methods, e.g. by photometric or fluorometric determination after UV excitation. An exemplary test system is described in US 2005/0214891, the disclosure of which is incorporated herein by reference in its entirety.

The present invention further relates also to an enzyme stabilized with a stable coenzyme, where the stabilized enzyme shows a decline in the enzymatic activity of less than 50%, typically less than 30% and in many cases less than 20% compared with the initial level, upon storage for at least 2 weeks, typically at least 4 weeks and in many cases at least 8 weeks at a temperature of at least 20° C., typically at least 25° C. and in many cases at least 30° C., where appropriate with high humidity, and also in certain embodiments so stored without a drying reagent.

The invention further relates also to a detection reagent for determining an analyte which comprises an enzyme stabilized with a stable coenzyme as indicated above. The invention additionally relates to a test element which comprises an enzyme stabilized according to the invention and a detection reagent, respectively, according to the invention. The detection reagent and the test element, respectively, may be suitable for carrying out dry or liquid tests. The test element in one embodiment comprises a test strip for fluorometric or photometric detection of an analyte. Such a test strip comprises the enzyme stabilized with a stable coenzyme and immobilized on an absorbent or/and swellable material such as, for instance, cellulose, plastics, etc.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIG. 21 is a depiction of the amino acid sequences of the glucose dehydrogenase double mutants GlucDH_E96G_E170K (SEQ ID NO: 1) and GlucDH_E170K_K252L (SEQ ID NO:2).

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Example 1

Figure 1A:
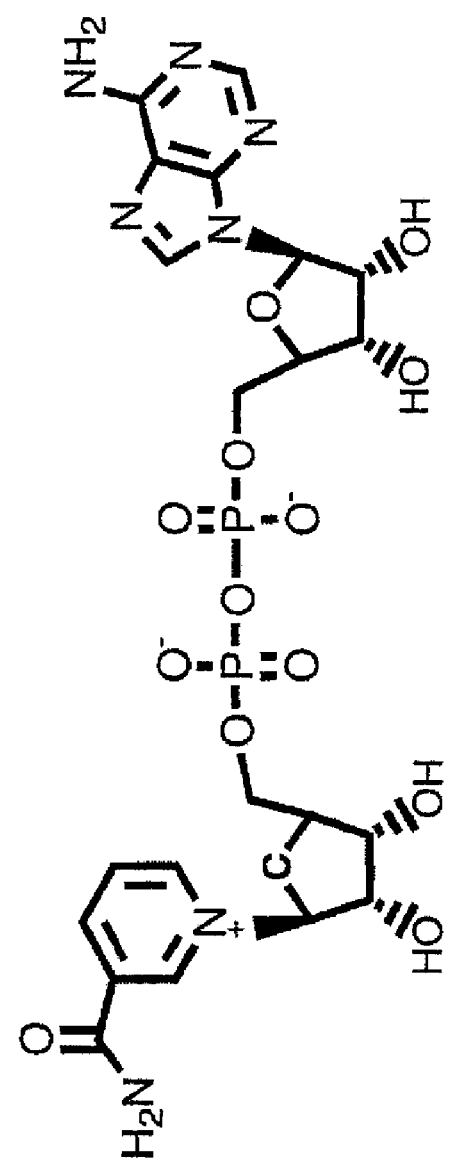
FIG. 1A is a depiction of the stable coenzyme carba-NAD (cNAD).
Figure 1B:
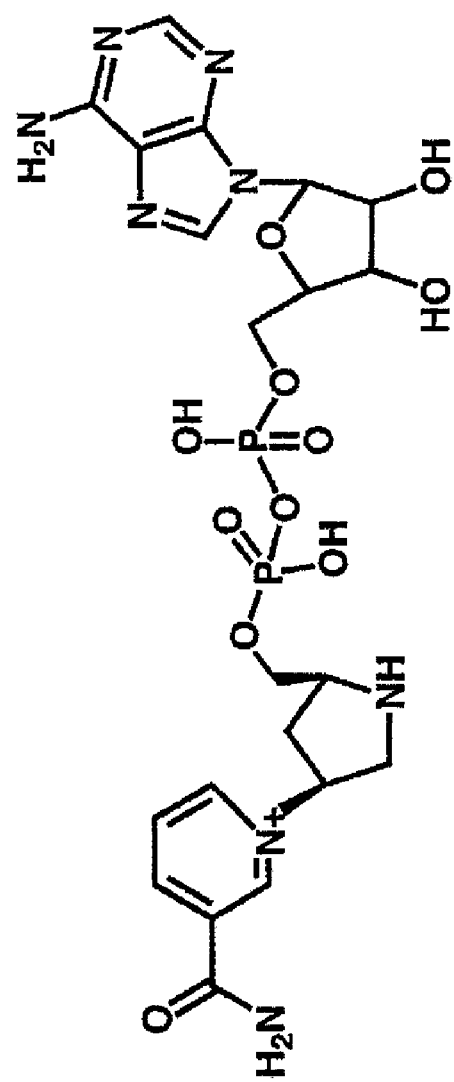
FIG. 1B is a depiction of the stable coenzyme pyrrolidinyl-NAD.

Carba-NAD (FIG. 1A) or NAD were added to the glucose-specific GlucDH. These formulations were in each case applied to Pokalon film (Lonza) and, after drying, stored under warm and moist conditions (32° C., 85% relative humidity). The reaction kinetics and the function plot were subsequently determined at regular intervals. In parallel, at each of the times of measurement a cNAD/NAD analysis and a determination of the residual activity of the enzyme were carried out.

Figure 2A:
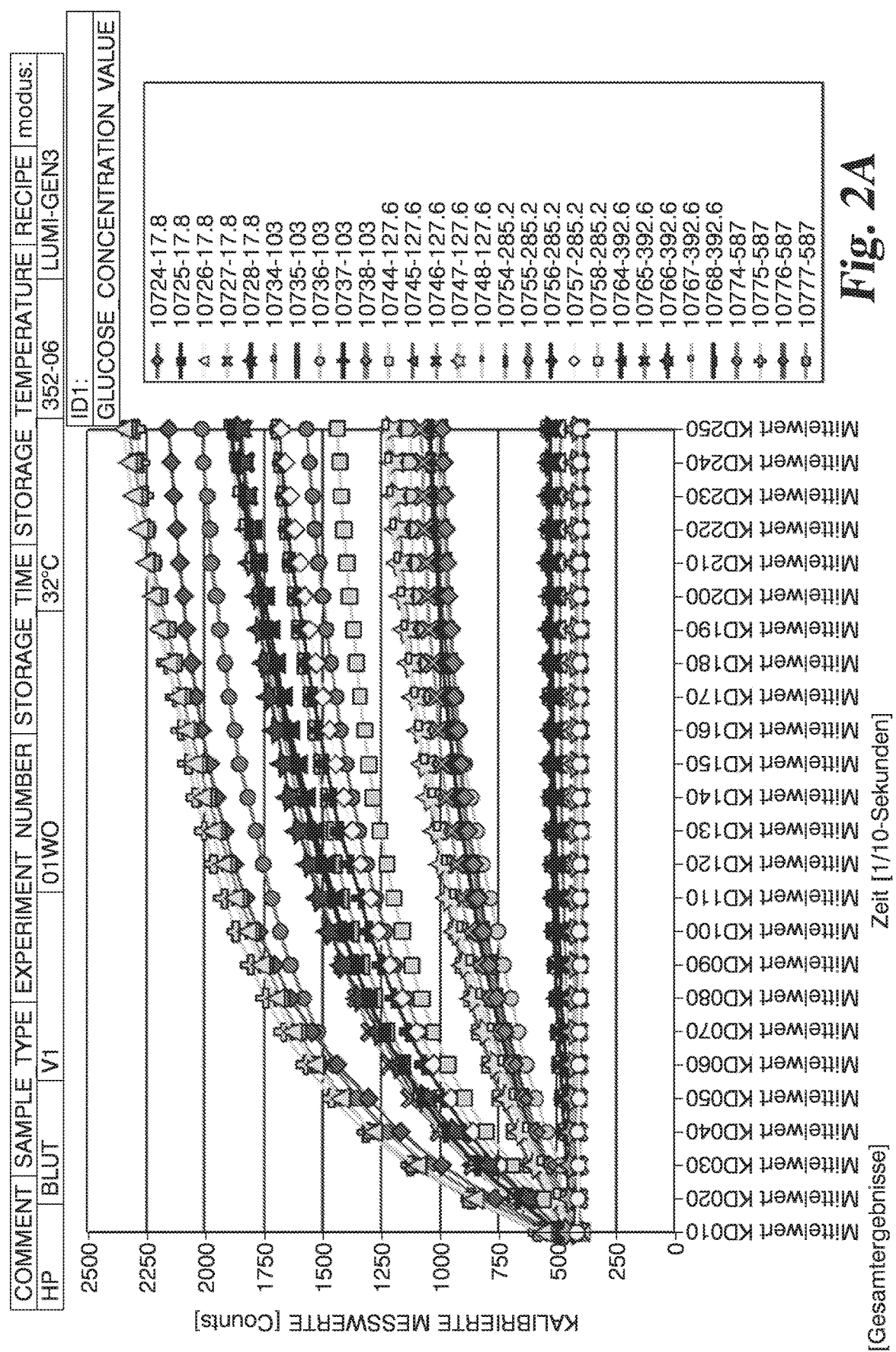
FIG. 2A depicts the results of the glucose dehydrogenase enzyme kinetics in the presence of NAD and in the presence of cNAD, respectively, before and after storage, specifically kinetics of GlucDH in the presence of NAD after 1 day.
Figure 2B:
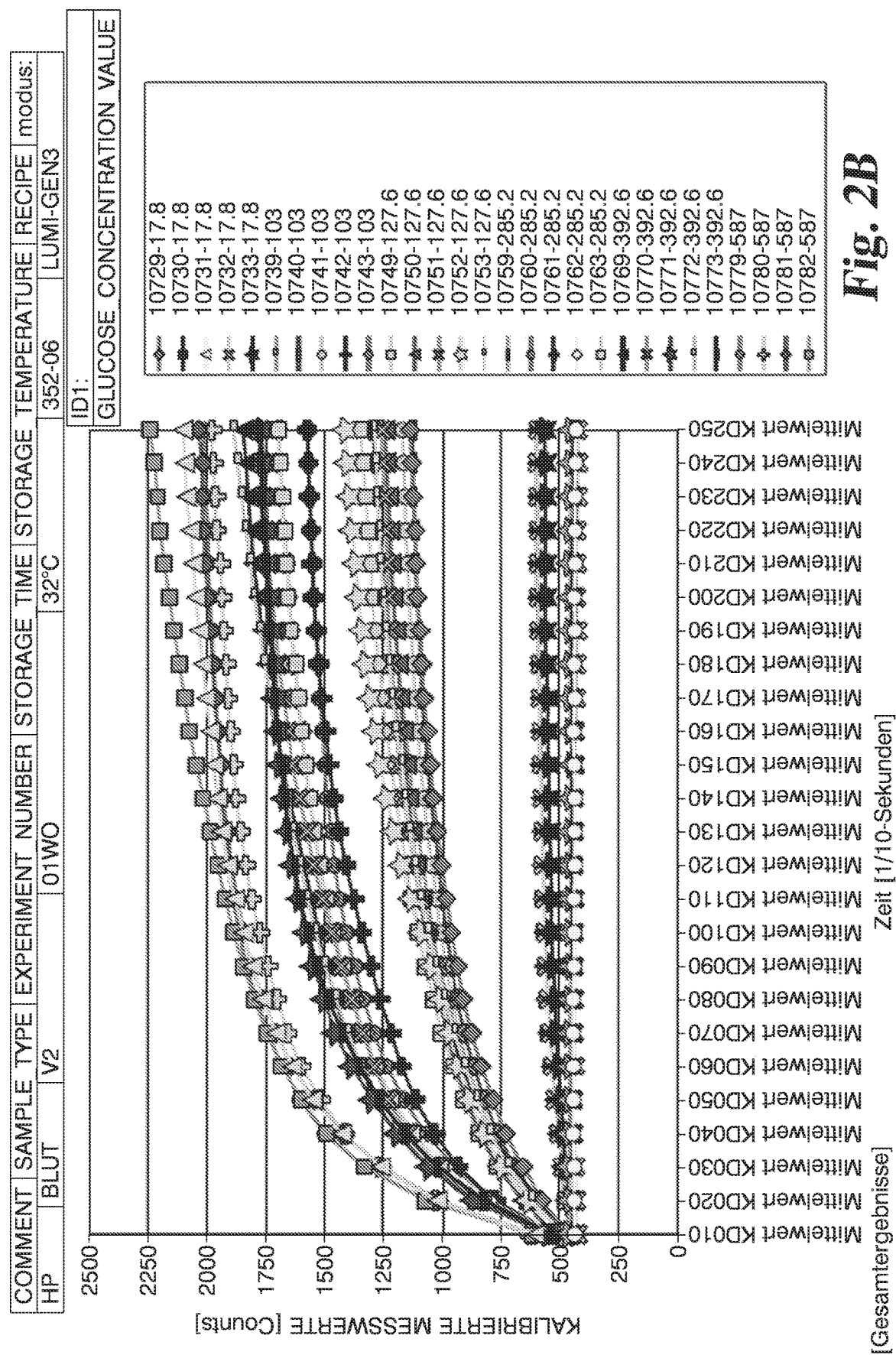
FIG. 2B depicts the results of the glucose dehydrogenase enzyme kinetics in the presence of NAD and in the presence of cNAD, respectively, before and after storage, specifically kinetics of GlucDH in the presence of cNAD after 1 day.
Figure 2C:
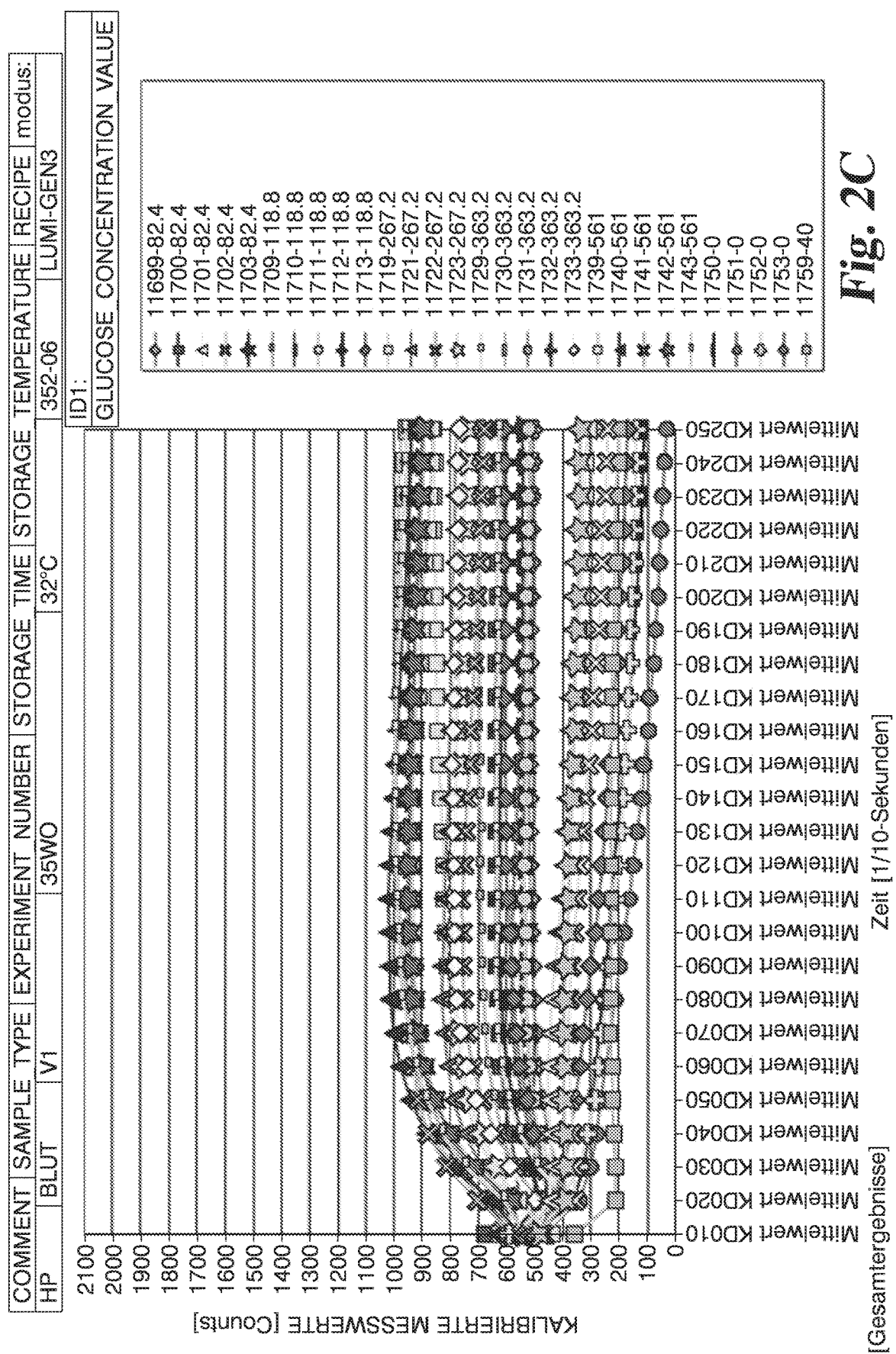
FIG. 2C depicts of the results of the glucose dehydrogenase enzyme kinetics in the presence of NAD and in the presence of cNAD, respectively, before and after storage, specifically kinetics of GlucDH in the presence of NAD after storage at 32° C. and 85% relative humidity for 5 weeks.
Figure 2D:
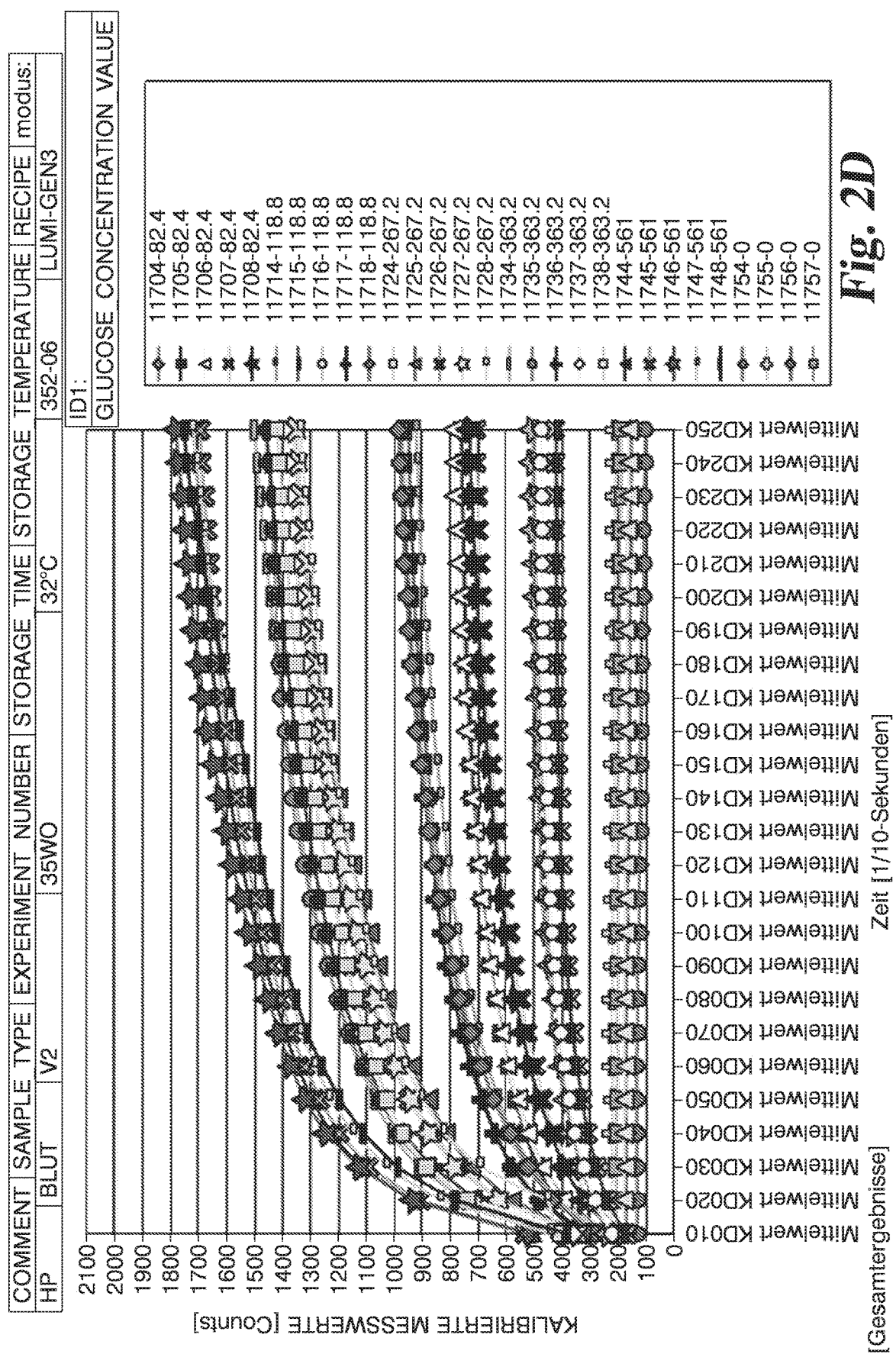
FIG. 2D depicts the results of the glucose dehydrogenase enzyme kinetics in the presence of NAD and in the presence of cNAD, respectively, before and after storage, specifically kinetics of GlucDH in the presence of cNAD after storage at 32° C. and 85% relative humidity for 5 weeks.

The kinetics plots for NAD (FIG. 2A) and cNAD (FIG. 2B) determined on the first day are comparable and also show a similar rise in the glucose dependence. However, a distinct difference in the kinetics plots is evident after 5 weeks. Whereas the kinetics for NAD (FIG. 2C) decrease greatly in their dynamics, the kinetics of the enzyme stabilized with cNAD remain virtually unchanged (FIG. 2D).

Figure 3:
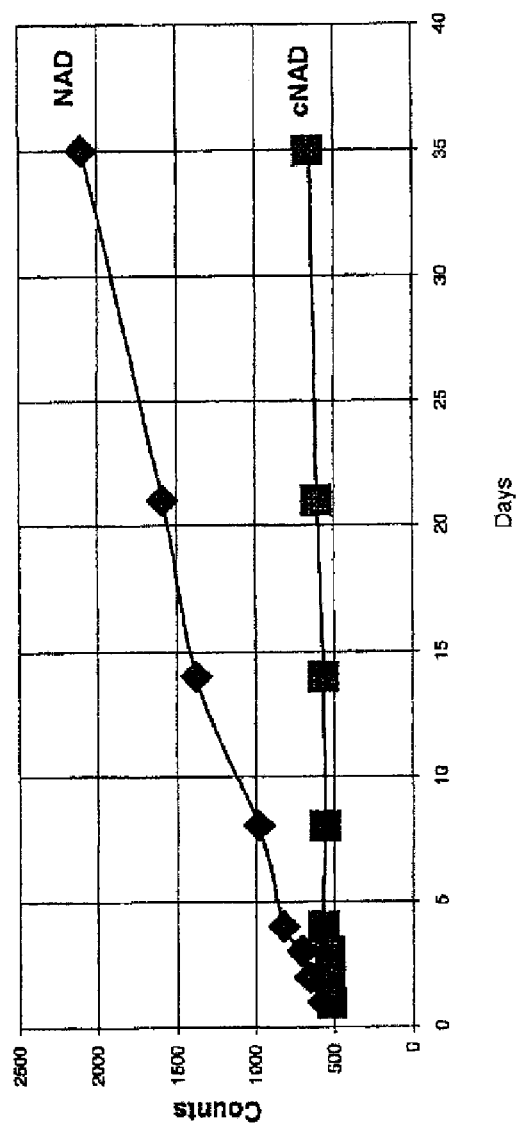
FIG. 3 is a comparison of the blank values for glucose dehydrogenase in the presence Of NAD and of GlucDH in the presence of cNAD, respectively, over a period of up to 5 weeks at 32° C. and 85% humidity.

There is also a distinct difference in the blank values (dry blank value before application of a blood sample), as is evident from FIG. 3. The rise in the dry blank value for NAD is attributable to the formation of fluorescent particles (Oppenheimer (1982), Supra). Surprisingly, this does not occur with cNAD.

Figure 4:
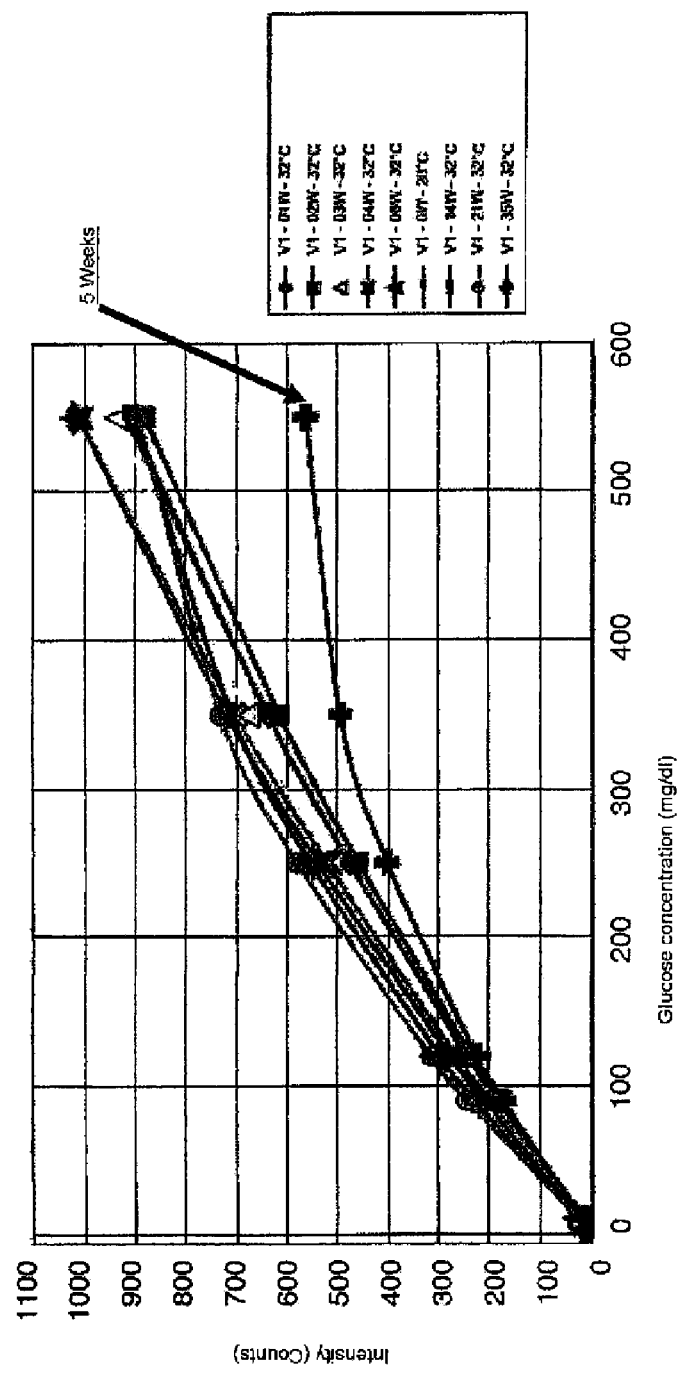
FIG. 4 is a depiction of various function plots of glucose dehydrogenase after storage of glucose dehydrogenase in the presence of NAD at 32° C. and 85% humidity. The storage time varied between 1 day and 5 weeks.
Figure 5A:
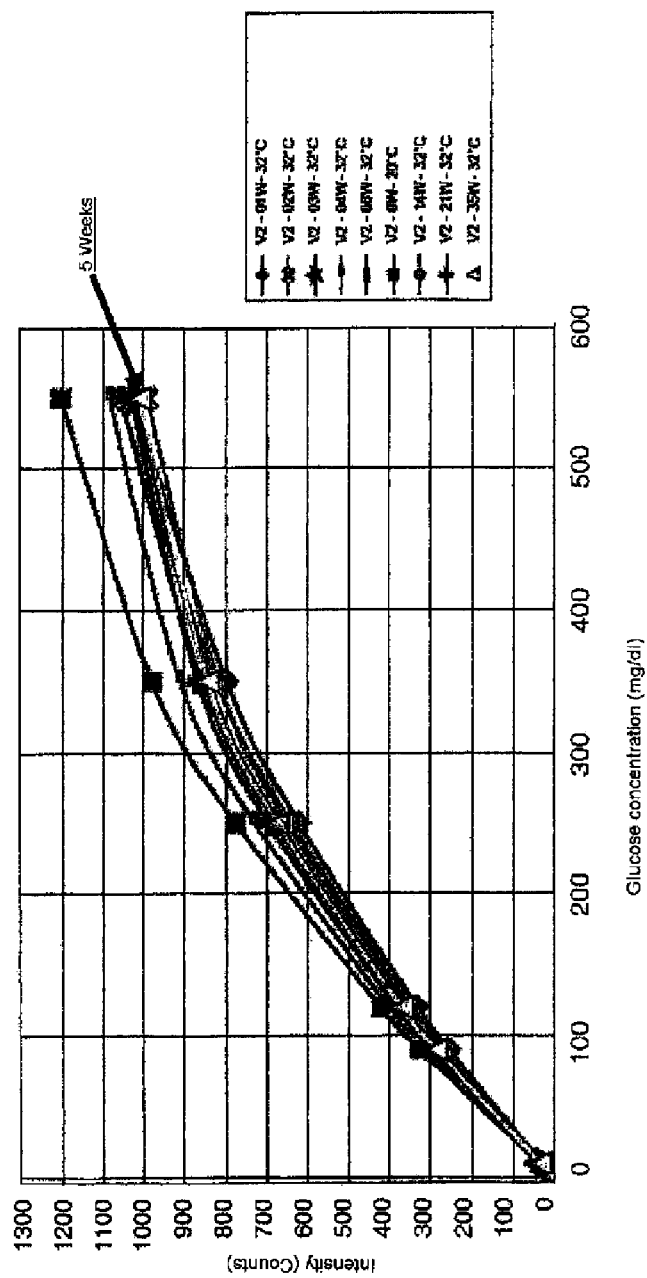
FIG. 5A is a depiction of a function plot of glucose dehydrogenase after storage of glucose dehydrogenase in the presence of cNAD at 32° C. and 85% humidity for a storage time varied between 1 day and 5 weeks.
Figure 5B:
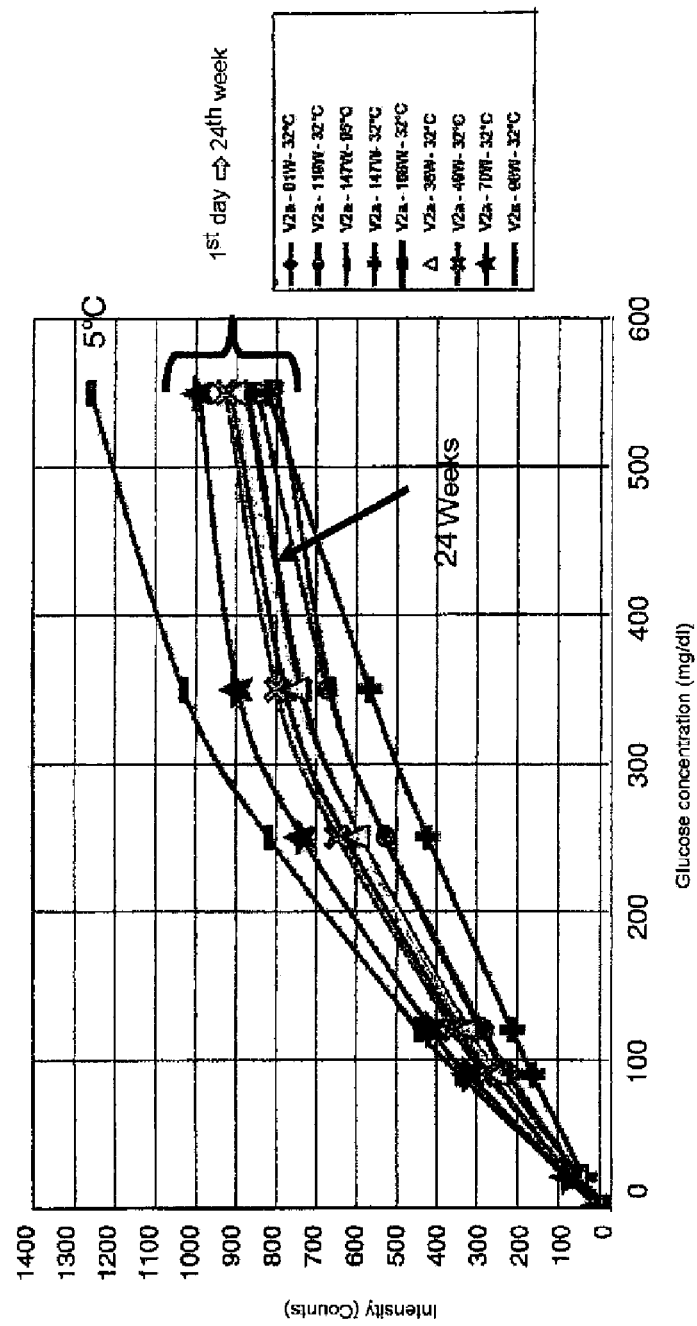
FIG. 5B is a depiction of a function plot of glucose dehydrogenase after storage of glucose dehydrogenase in the presences of cNAD at 32° C. and 85% humidity between 1 day and 24 weeks.

The differing stability of glucose dehydrogenase in the presence of NAD and cNAD, respectively, is also evident from comparison of FIGS. 4 and 5. After 5 weeks, the function plot for the enzyme stabilized with cNAD is still in the bunch of previous measurements (Figure SA), whereas the plot for the enzyme treated with NAD (FIG. 4) shows a fall-off at higher concentrations, which is a typical sign that the amounts of enzyme/coenzyme are too low. FIG. 5B shows various function plots of the glucose dehydrogenase stabilized with cNAD over a period of 24 weeks. It is clear in this connection that the function of the enzyme is only slightly changed at high glucose concentrations throughout the period and approximately corresponds after 24 weeks to the value obtained after 5 weeks.

Figure 6:
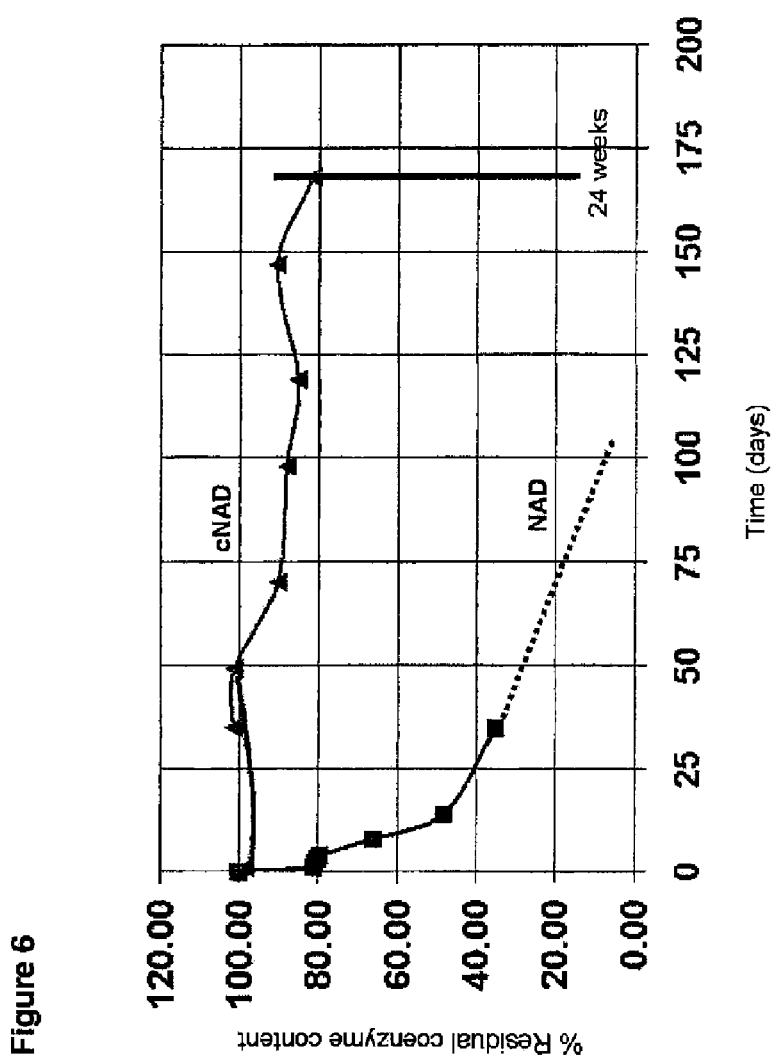
FIG. 6 is a depiction of the residual content of NAD and cNAD after storage of glucose dehydrogenase in the presence of NAD and cNAD, respectively, at 32° C. and 85% humidity for 24 weeks.

The relation between structure of the coenzyme and its stability over a predetermined period is evident from FIG. 6. According to this, the residual content of cNAD in a glucose detection reagent after storage (at 32° C. and 85% relative humidity) for 24 weeks is still about 80% of the initial level, whereas the content of NAD in a glucose detection reagent stabilized with NAD declines after only 5 weeks to about 35% of the initial level and, by extrapolation, is reduced to zero after about 17 weeks.

Figure 7A:
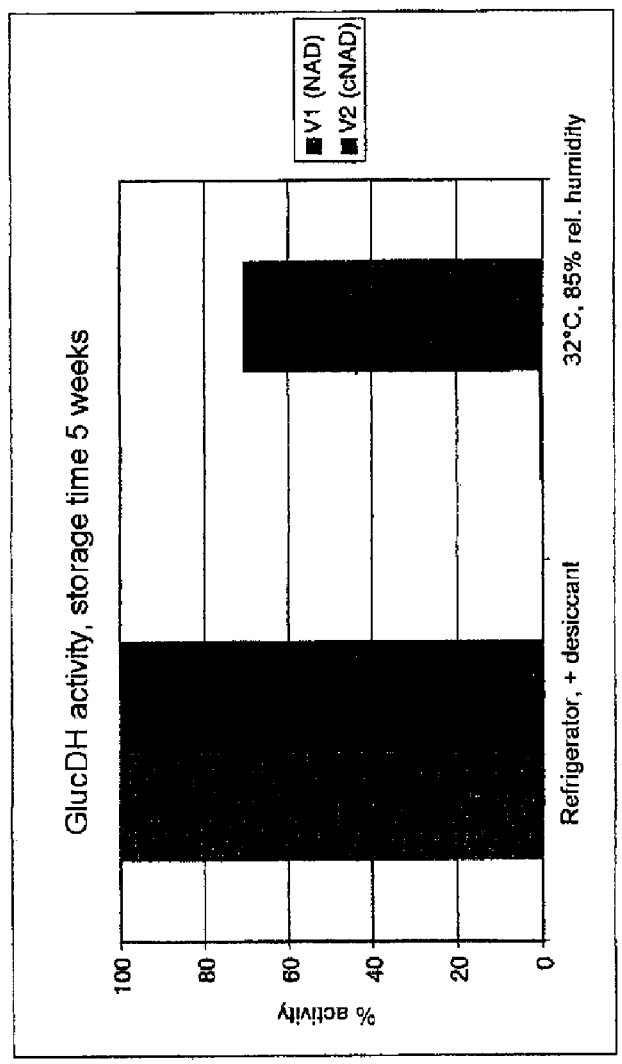
FIG. 7A is a depiction of the GlucDH activity after storage of glucose dehydrogenase in the presence of NAD and cNAD, respectively, at 32° C. and 85% humidity for 5 weeks.
Figure 7B:
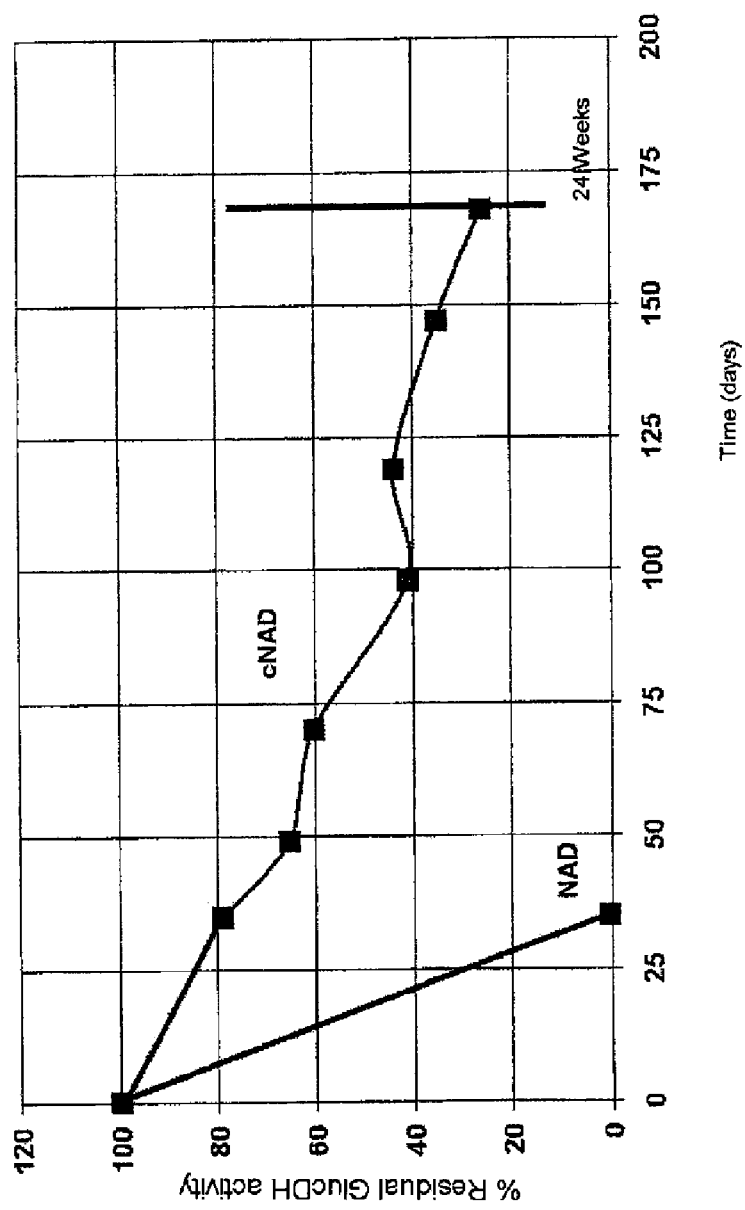
FIG. 7B is a depiction of the GlucDH activity after storage of glucose dehydrogenase in the presence of NAD and cNAD at 32° C. and 85% humidity for 24 weeks.

The result of the determination of residual activity of the active GlucDH enzyme after 5 weeks at 32° C. and 85% relative humidity (FIG. 7A) is completely surprising. The enzyme stabilized with NAD now shows only an extremely low enzyme activity (0.5%), whereas the enzyme stabilized with cNAD still has a residual activity of 70% (in each case by comparison with samples stored in a refrigerator with desiccant). After 24 weeks at 32° C. and 85% relative humidity (FIG. 7B), the residual activity of the enzyme on stabilization with cNAD is still about 25%.

Figure 8:
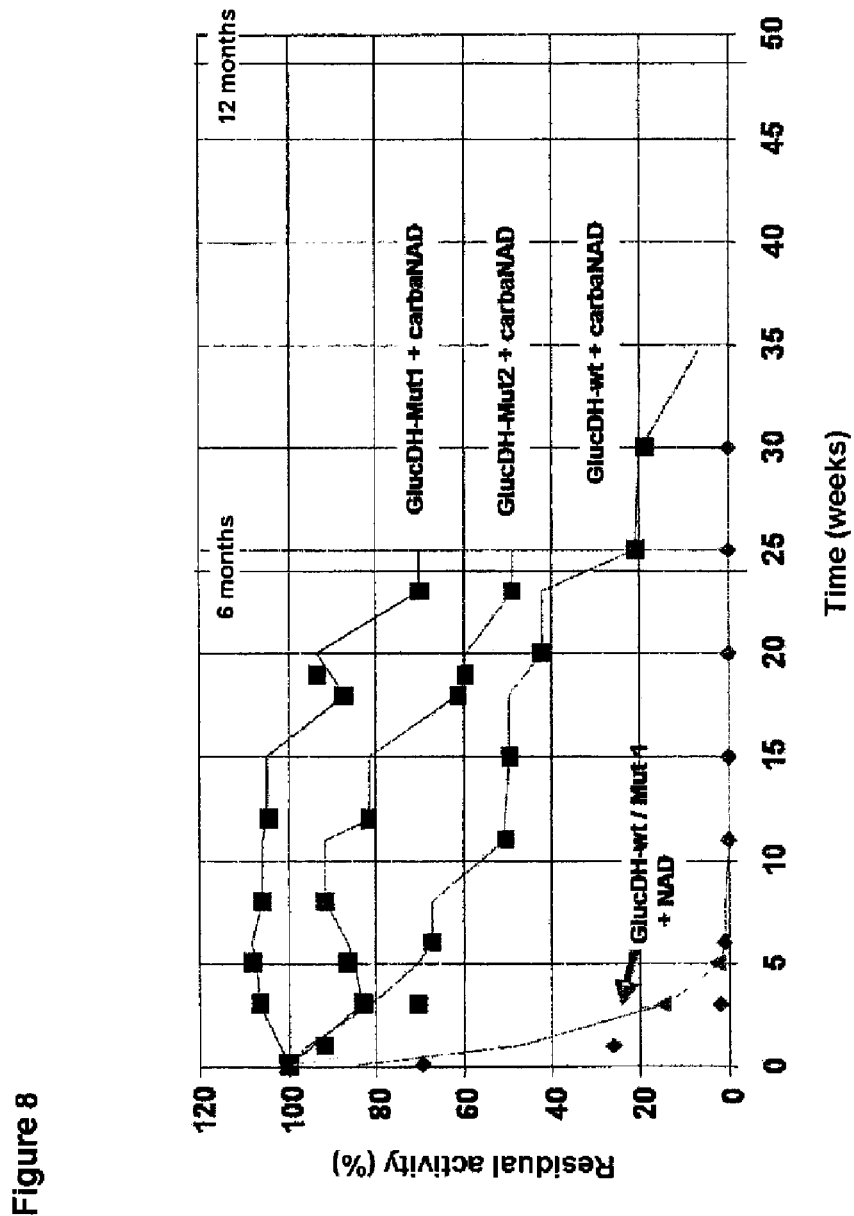
FIG. 8 is a depiction of the GlucDH activity after storage of glucose dehydrogenase (GlucDH wt), the double mutant GlucDH_E96G_EI70K (GlucDH Mut1) and the double mutant GlucDH_E170K_K252L (GlucDH Mut2) in the presence of NAD and cNAD, respectively, at 32° C. and 83% relative humidity over a period of 25 weeks.

If a mutant is used instead of the wild-type enzyme (from *Bacillus subtilis*), it is possible to increase the residual GlucDH activity even further. After storage at 32° C. and 85% relative humidity in the presence of cNAD for 24 weeks, the residual activity of a GlucDH_E96G_E170K mutant with the amino acid replacements glutamic acid→glycine at position 96 and glutamic acid→lysine at position 170 (GlucDH-Mut1) of the wild-type enzyme is about 70%, whereas the residual activity of a GlucDH_E170K_K252L mutant with the amino acid replacements glutamic acid→lysine at position 170 and lysine→leucine at position 252 (GlucDH-Mut2) is about 50% (FIG. 8).

Figure 9:
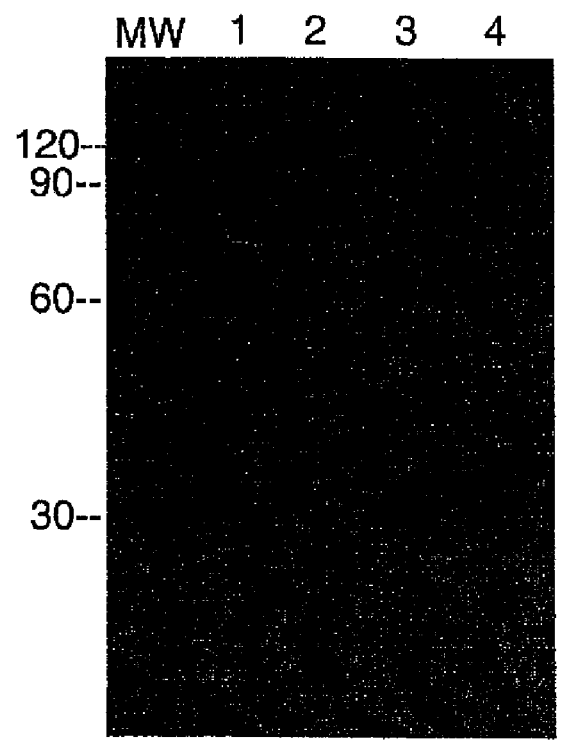
FIG. 9 shows an analysis of glucose dehydrogenase by gel electrophoresis after storage in the presence of NAD and cNAD, respectively. Test conditions: MW, 10 220 kDa markers; 1: GlucDH/NAD, 5 weeks at 6° C.; 2: GlucDH/NAD, 5 weeks at 32° C./85% relative humidity; 3: GlucDH/cNAD, 5 weeks at 6° C.; 4: GlucDH/cNAD, 5 weeks at 32° C./85% relative humidity.
Figure 10:
FIG. 10 shows an analysis of glucose dehydrogenase by gel electrophoresis after storage at 50° C. in the presence of NAD and cNAD, respectively. Test conditions: MW, 10 220 kDa markers; 1: GlucDH 8.5 mg/ml, NAD, 0 hours; 2: GlucDH 8.5 mg/ml, NAD, 22 hours; 3: GlucDH 8.5 mg/ml, NAD, 96 hours; 4: GlucDH 8.5 mg/ml, NAD, 118 hours; 5: GlucDH 8.5 mg/ml, NAD, 140 hours; 6: GlucDH 8.5 mg/ml, NAD, 188 hours; 7: GlucDH 8.5 mg/ml, NAD, 476 hours; 8: GlucDH 8.5 mg/ml, cNAD, 0 hours; 9: GlucDH 8.5 mg/ml, cNAD, 188 hours; 10: GlucDH 8.5 mg/ml, cNAD, 476 hours.

The analysis of glucose dehydrogenase by gel electrophoresis in an SDS gel (FIGS. 9 and 10) also shows clearly the difference between storage in the presence of NAD and cNAD, respectively. Whereas the enzyme is still identifiable as a band with the expected mobility after storage for 5 weeks at 32° C. and 85% relative humidity in the presence of cNAD, the enzyme stored in the presence of NAD has completely disappeared (FIG. 9). It is evident at the same time from FIG. 10 that the band of the enzyme stabilized by NAD and stored at 50° C. becomes weaker as the storage time increases and has virtually disappeared after 476 hours, whereas the corresponding band of the enzyme stored in the presence of cNAD shows an only slight change compared with a band detected at the start of the experiment.

Figure 11A:
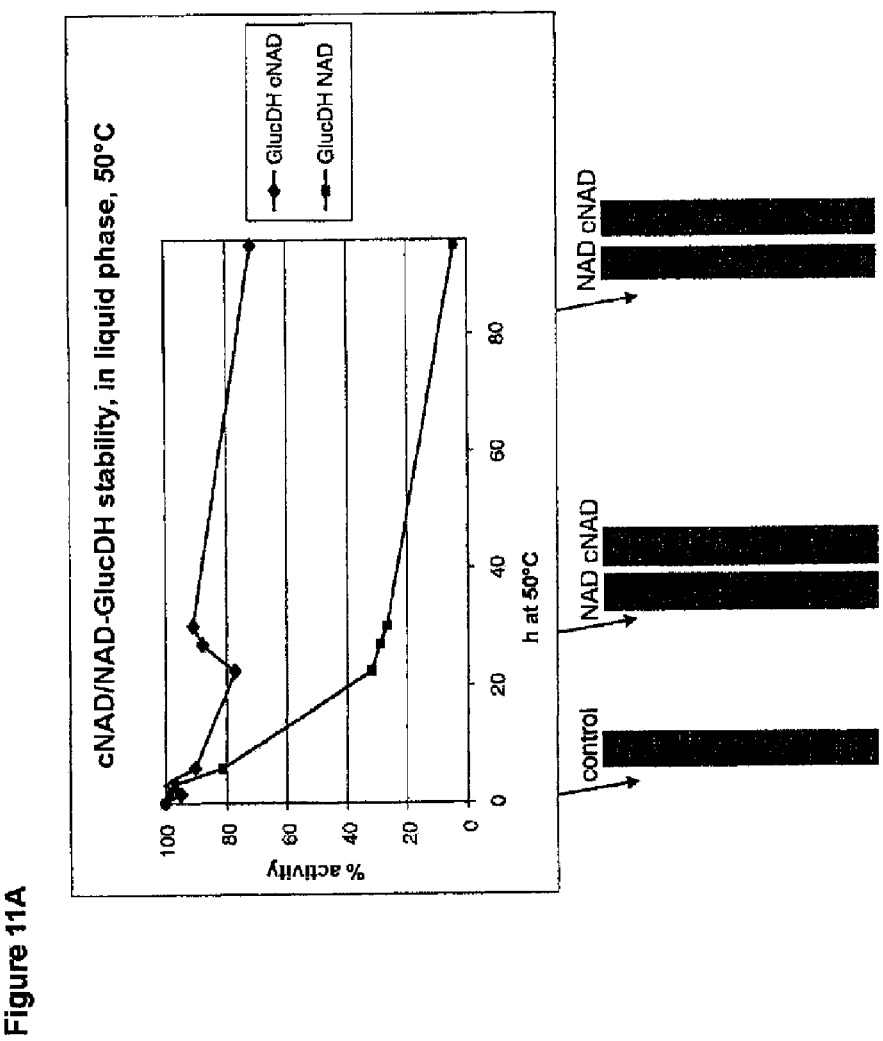
FIG. 11A is a depiction of the stability of glucose dehydrogenase in the presence of NAD and cNAD, respectively, in liquid phase at 50° C. over a period of 4 days Test conditions: GlucDH 10 mg/ml; NAD and cNAD, respectively, 12 mg/ml; buffer: 0.1 M Tris, 1.2 M NaCl, pH 8.5; temperature 50° C.
Figure 11:
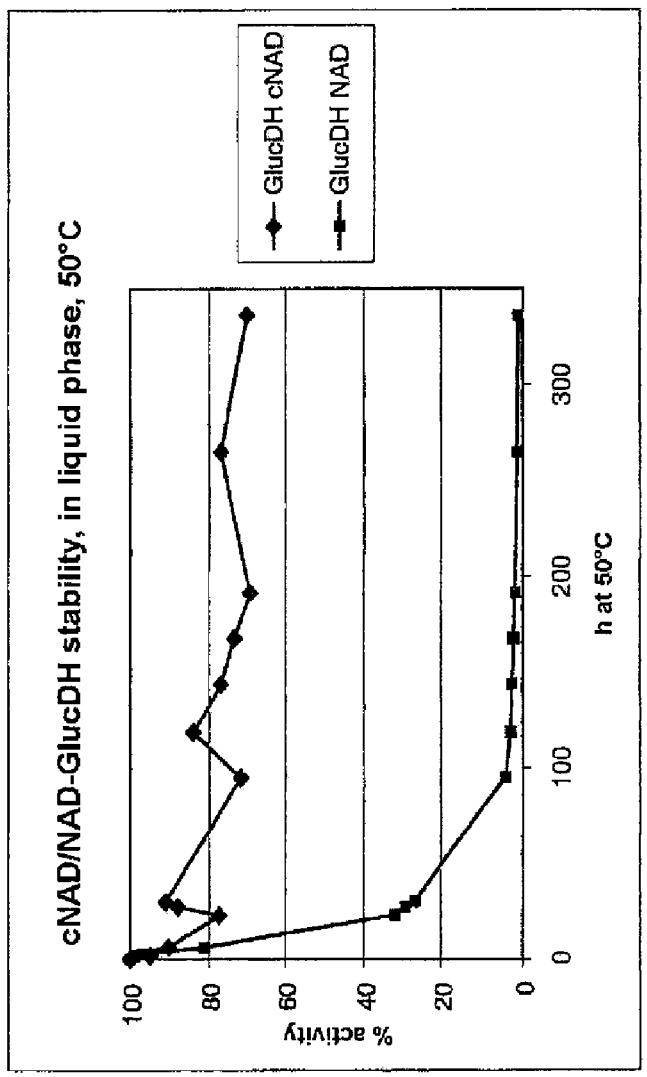
FIG. 11B is a depiction of the stability of glucose dehydrogenase in the presence of NAD and cNAD, respectively, in liquid phase at 50° C. over a period of 14 days at the same test conditions as FIG. 11A.

This result can also be confirmed on storage in liquid phase (FIGS. 11A and 11B). After 95 hours at 50° C., the residual activity of glucose dehydrogenase in the presence of the native coenzyme NAD is ≈5%, whereas the residual activity of GlucDH in the presence of the artificial coenzyme cNAD is 75% (FIG. 11A). After storage at 50° C. for 336 hours, the residual activity of the enzyme stabilized with NAD is now only about 1%; the residual activity of the enzyme stored in the presence of cNAD is observed to be still about 70%. The corresponding SDS gels likewise show a change in the GlucDH band in the presence of the native coenzyme NAD: new bands appear at higher molecular masses and there is a shift in the 30 kDa band.

Overall, it is an extremely surprising result that stabilization of the cofactor simultaneously brings about a stabilization of the enzyme—and not just through the cooperative effect of the better cohesion of the enzyme. Decomposition of the cofactor NAD has a negative effect on the stability of the enzyme GlucDH and in fact speeds up inactivation thereof. Replacement of native NAD by artificial analogues permits GlucDH to be stored under stress conditions (e.g. elevated temperature) even in the presence of a cofactor.

It is possible with such a system to produce blood glucose test strips with considerably improved stability properties, for which a presentation without desiccant is possible.

Example 2 cNAD or NAD were added to an alcohol detection solution. These mixtures were stored at 35° C. The stability of the enzyme was then checked at regular intervals, and the residual activity of the enzyme was determined.

Figure 12:
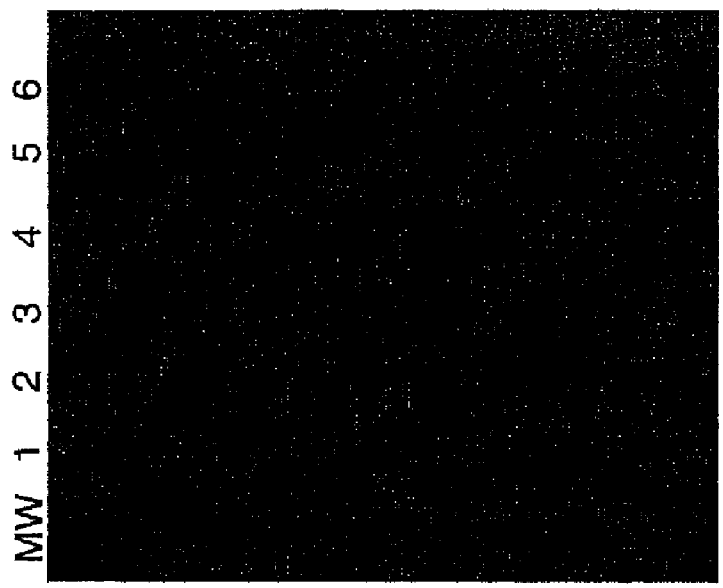
FIG. 12 shows an analysis of alcohol dehydrogenase from yeast by gel electrophoresis after storage in the presence of NAD and cNAD, respectively. Test conditions: MW, 10 220 kDa markers; 1: ADH, 65 hours at 6° C.; 2: ADH/cNAD, 65 hours at 6° C.; 3: ADH/NAD, 65 hours at 6° C.; 4: ADH, 65 hours at 35° C.; 5: ADH/cNAD, 65 hours at 35° C.; 6: ADH/NAD, 65 hours at 35° C.

Once again, an analysis by gel electrophoresis in an SDS gel (FIGS. 12 and 13) shows the difference between storage in the presence of NAD and cNAD. Thus, the bands of the alcohol dehydrogenase stabilized with cNAD differ only slightly after storage at 6° C. and 35° C., respectively, for 65 hours, indicating a stabilization of the enzyme by artificial coenzyme. By contrast, the band of the enzyme stored in the presence of NAD at 35° C. has completely disappeared (FIG. 12).

Figure 13:
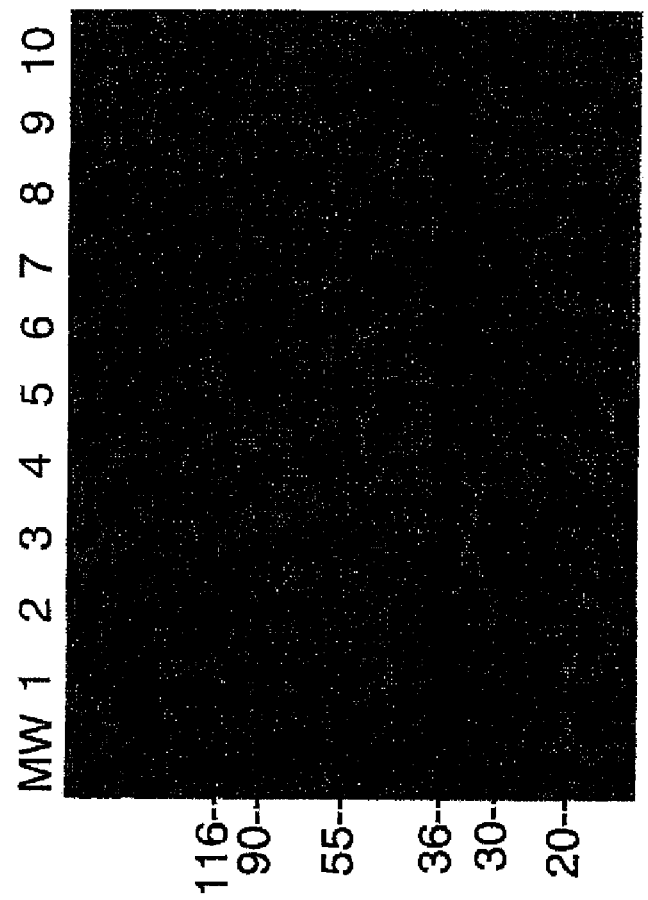
FIG. 13 shows an analysis of alcohol dehydrogenase from yeast by gel electrophoresis after storage at 35° C. in the presence of NAD and cNAD, respectively. Test conditions: MW, 10 220 kDa markers; 1: ADH/NAD, 0 days; 2: ADH/NAD, 1 day; 3: ADH/NAD, 2 days; 4: ADH/NAD, 3 days; 5: ADH/NAD, 5 days; 6: ADH/cNAD, 0 days; 7: ADH/cNAD, 1 day; 8: ADH/cNAD, 2 days; 9: ADH/cNAD, 3 days; 10: ADH/cNAD, 6 days.

It is further clear from FIG. 13 that the band of the enzyme stabilized with NAD and stored at 35° C. becomes weaker as the storage time increases and has almost completely disappeared after 5 days. A band of the enzyme stabilized with cNAD detected after storage at 35° C. for 6 days shows distinctly less decomposition of the enzyme and thus an increased stability.

Figure 14:
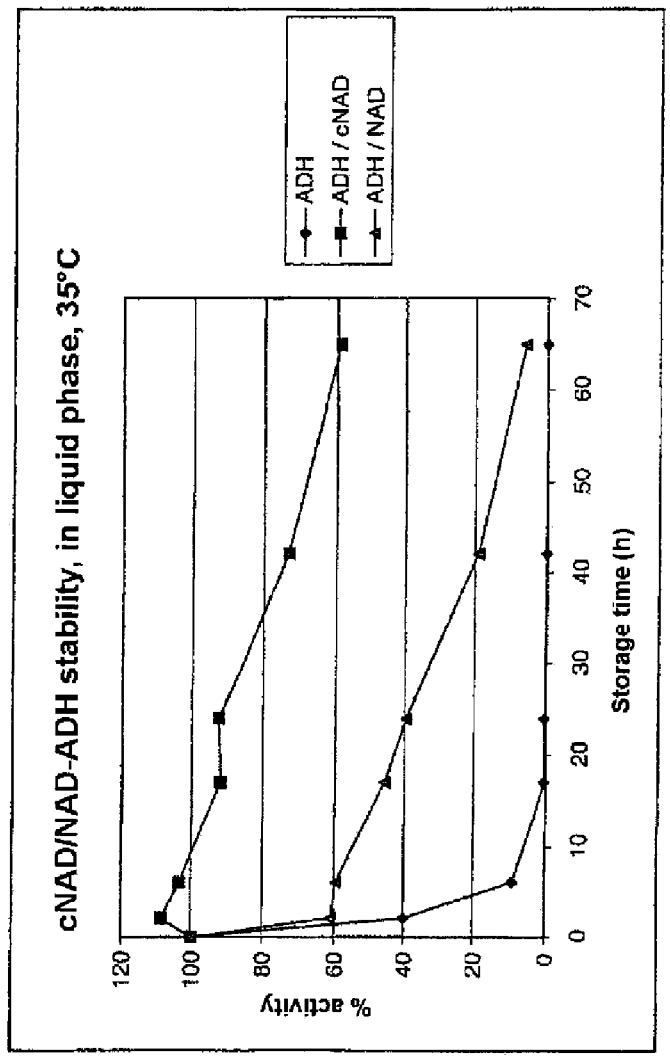
FIG. 14 is a depiction of the stability of alcohol dehydrogenase from yeast in the presence of NAD and cNAD, respectively, in liquid phase at 35° C. over a period of 65 hours. Test conditions: ADH 5 mg/ml; NAD and cNAD, respectively, 50 mg/ml; buffer: 75 mM Na4P2O7, glycine, pH 9.0; temperature 35° C.

This result can be confirmed also on storage in liquid phase (FIG. 14). After 65 hours at 35° C., the residual activity of alcohol dehydrogenase in the presence of the native coenzyme NAD is about 6%, whereas the residual activity of the enzyme in the presence of the artificial coenzyme cNAD is still about 60%.

Example 3

To determine glucose, various test systems which included in each case glucose dehydrogenase, NAD, a mediator and, where appropriate, an optical indicator were measured photometrically and electrochemically.

For photometric measurements, initially four test elements which had in each case been stored at room temperature for 11 weeks and comprised 2,18-phosphomolybdic acid, besides glucose dehydrogenase, NAD and a mediator, were investigated with various glucose concentrations.

Figure 15:
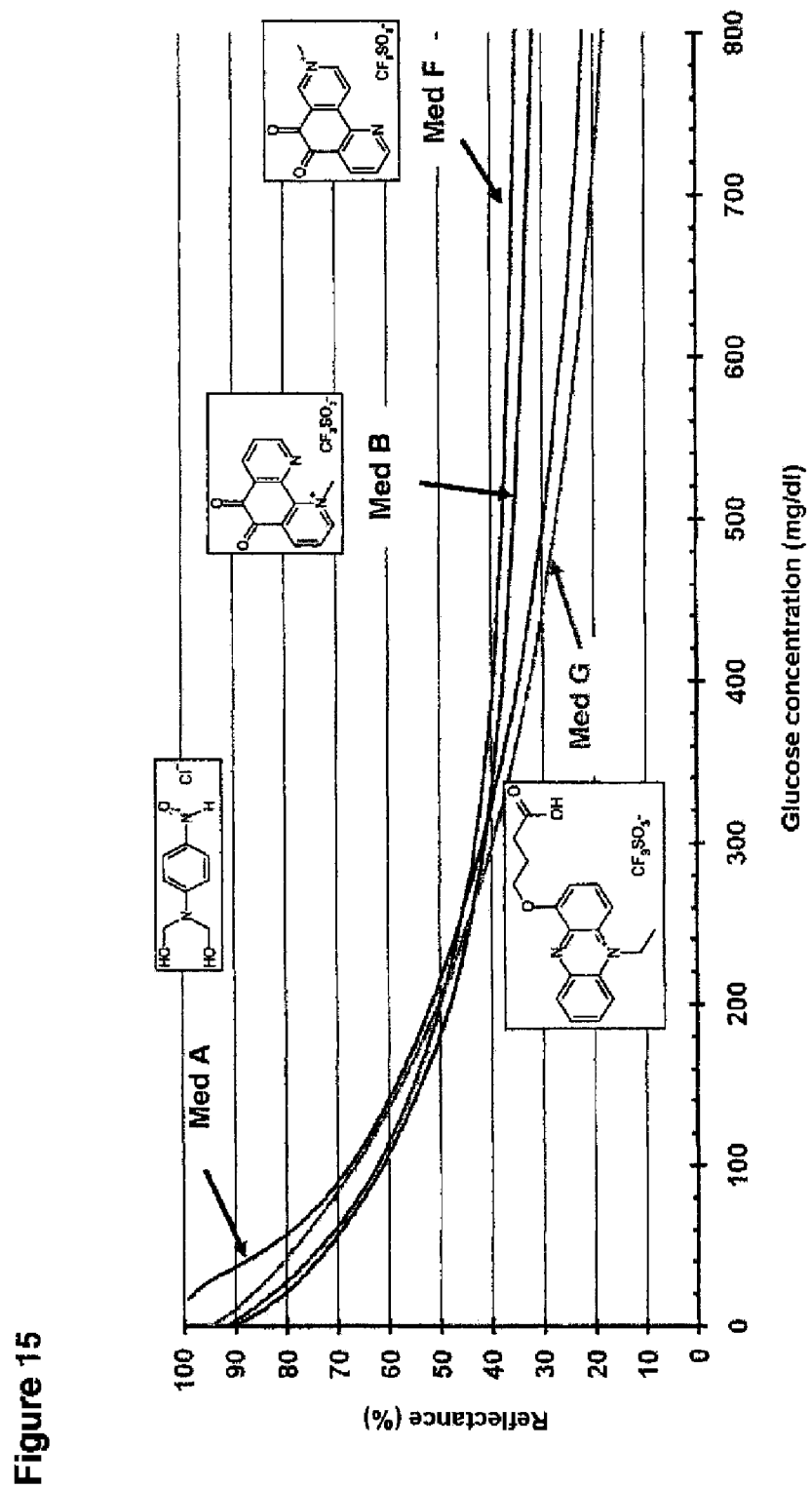
FIG. 15 is a depiction of various function plots of glucose dehydrogenase after storage in the presence of NAD and various mediators at room temperature for 11 weeks.

As is evident from FIG. 15, a fall in the reflectance was observed with increasing glucose concentration for all four mediators employed, i.e. [(4-nitrosophenyl)imino]dimethanol hydrochloride (Med A), 1-methyl-5,6-dioxo-5,6-dihydro-1, 10-phenanthrolinium trifluoromethanesulfonate (Med B), 7-methyl-5,6-dioxo-5,6-dihydro-1, 7-phenanthrolinium trifluoromethanesulfonate (Med F) and 1-(3-carboxypropoxy)-5-ethylphenazinium trifluoromethanesulfonate (Med G), and thus the abovementioned mediators are in principle suitable for determining glucose by photometry.

Figure 16:
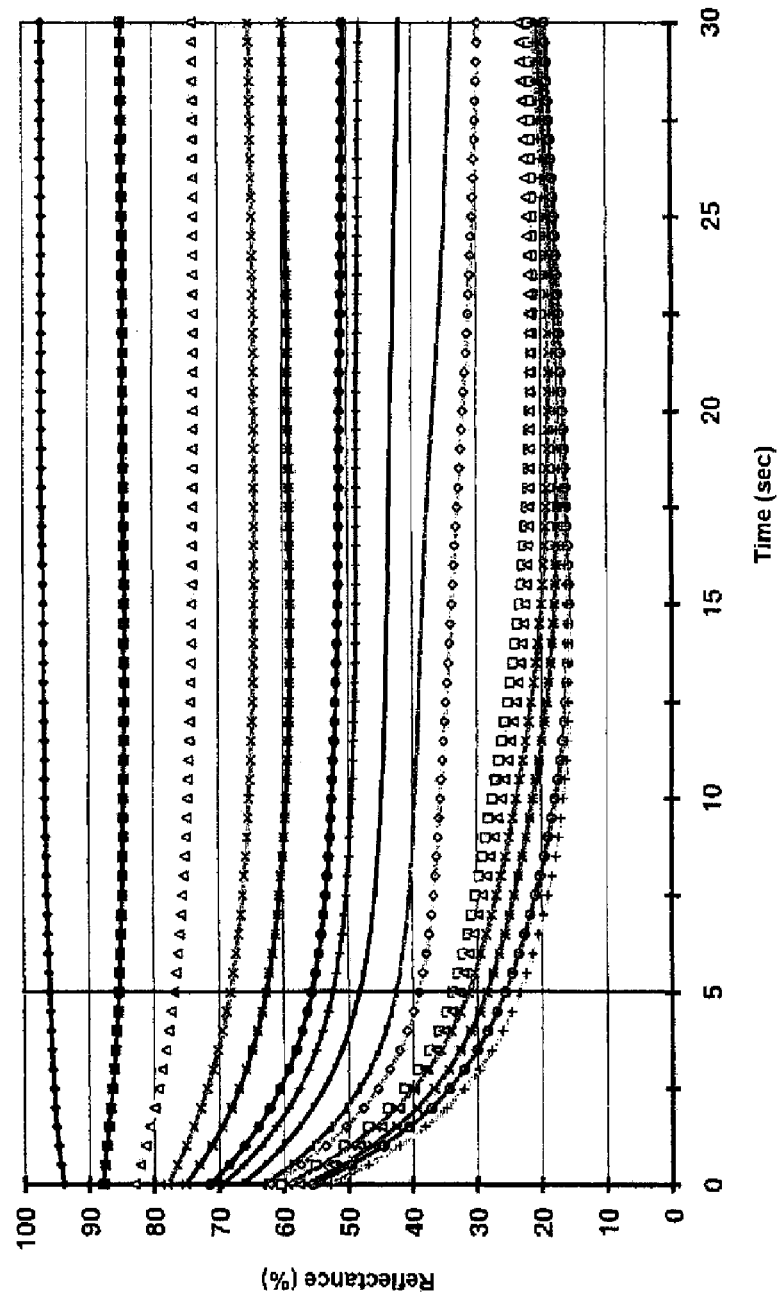
FIG. 16 is a depiction of the results of the glucose dehydrogenase enzyme kinetics in the presence of NAD and 1-(3-carboxypropoxy)-5-ethylphenazinium trifluoro-methanesulfonate at various glucose concentrations.

At high glucose concentrations in the region of 800 mg/dl, the reflectance of the measured sample on use of [(4-nitrosophenyl)imino]dimethanol hydrochloride and 1-(3-carboxypropoxy)-5-ethylphenazinium trifluoromethanesulfonate, respectively, is still about 20%, suggesting that these two mediators are particularly suitable for photometric measurements using the glucose dehydrogenase/NAD system, and thus also the glucose dehydrogenase/cNAD system. The kinetics of the conversion of glucose using the glucose dehydrogenase, NAD, 1-(3-carboxypropoxy)-5-ethylphenazinium trifluoromethanesulfonate and 2,18-phosphomolybdic acid system at glucose concentrations in the range from 0 to 800 mg/dl are depicted in FIG. 16.

Figure 17:
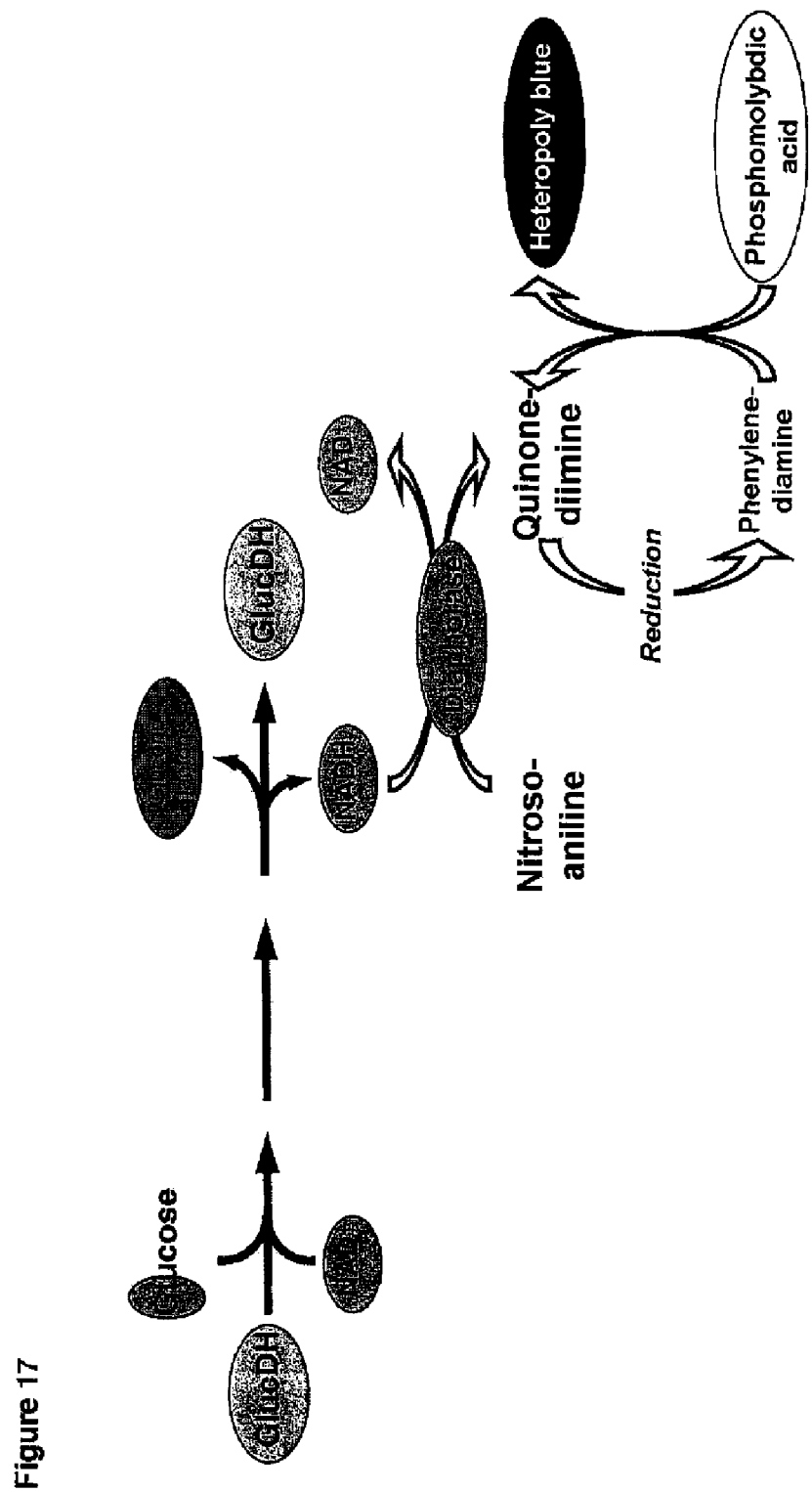
FIG. 17 is a diagrammatic depiction of glucose detection with GlucDH as enzyme and diaphorase as mediator.
Figure 18:
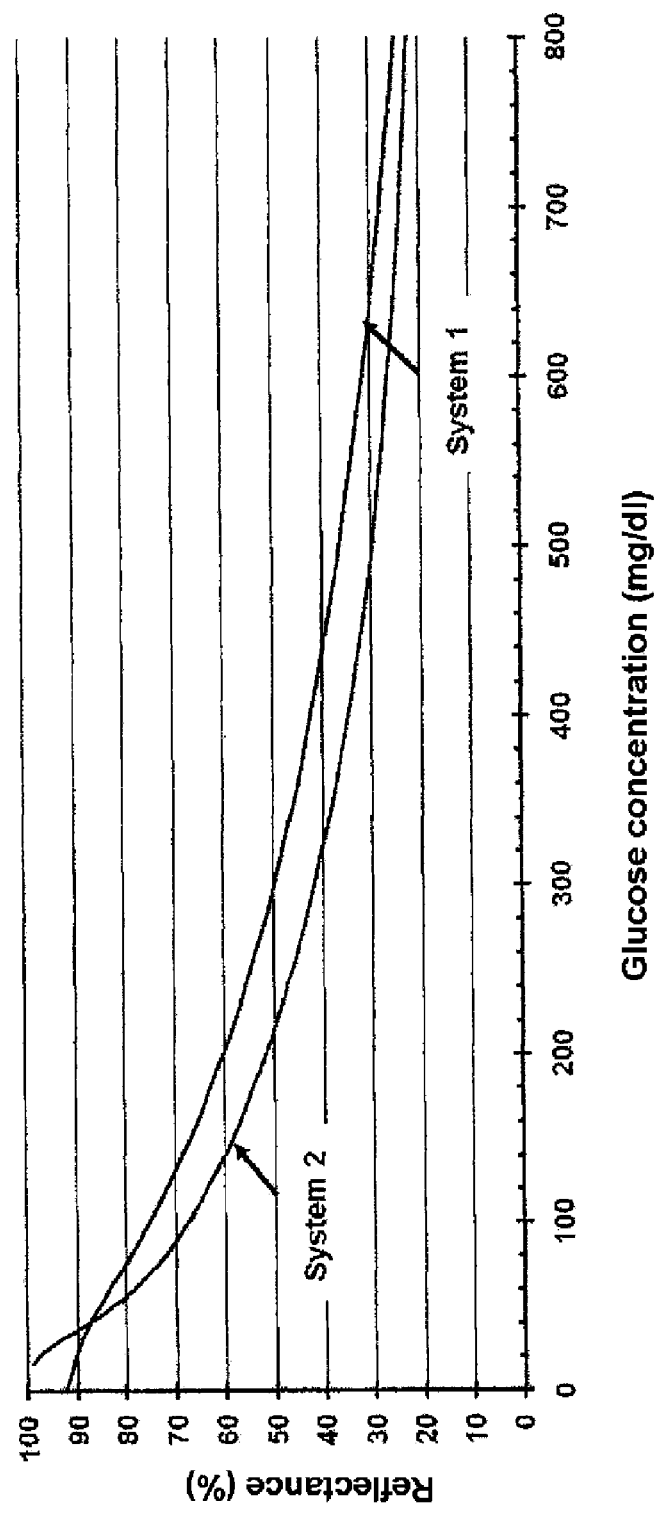
FIG. 18 is a depiction of the function plots of glucose dye oxidoreductase (GlucDOR) in the presence of pyrroloquinolinequinone (PQQ) and [(4-nitroso-phenyl)imino]dimethanol hydrochloride as mediator, and of glucose dehydrogenase in the presence of NAD and diaphorase/[(4-nitrosophenyl)imino]dimethanol hydrochloride as mediator, respectively.
Figure 19:
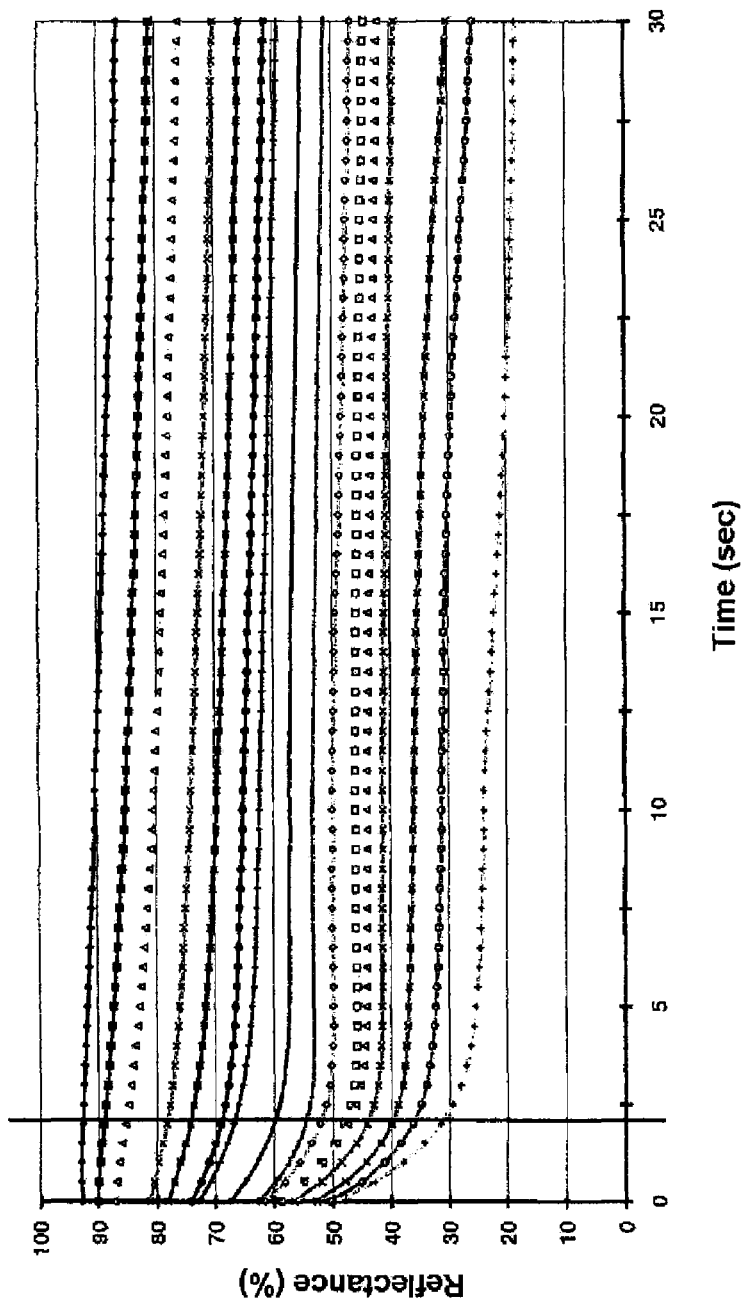
FIG. 19 is a depiction of the results of the glucose dehydrogenase enzyme kinetics in the presence of NAD and diaphorase at various glucose concentrations.

As is evident from the diagrammatic depiction in FIG. 17, the photometric determination of glucose can also take place with (additional) use of diaphorase as intermediary mediator. FIG. 18 shows a concentration-dependent decrease in reflectance for the glucose dehydrogenase, NAD, diaphorase, [(4-nitrosophenyl)imino]di methanol hydrochloride and 2,18-phosphomolybdic acid system (system 1). The system which served as comparison was glucose dye oxidoreductase, pyrroloquinolinequinone, [(4-nitrosophenyl)imino]dimethanol hydrochloride and 2, 18-phosphomolybdic acid (system 2), which likewise causes a concentration-dependent decrease in the reflectance, but has disadvantages because of the low specificity of glucose dye oxidoreductase. The kinetics of the conversion of glucose using system 1 at glucose concentrations in the range from 0 to 800 mg/dl are depicted in FIG. 19.

Figure 20:
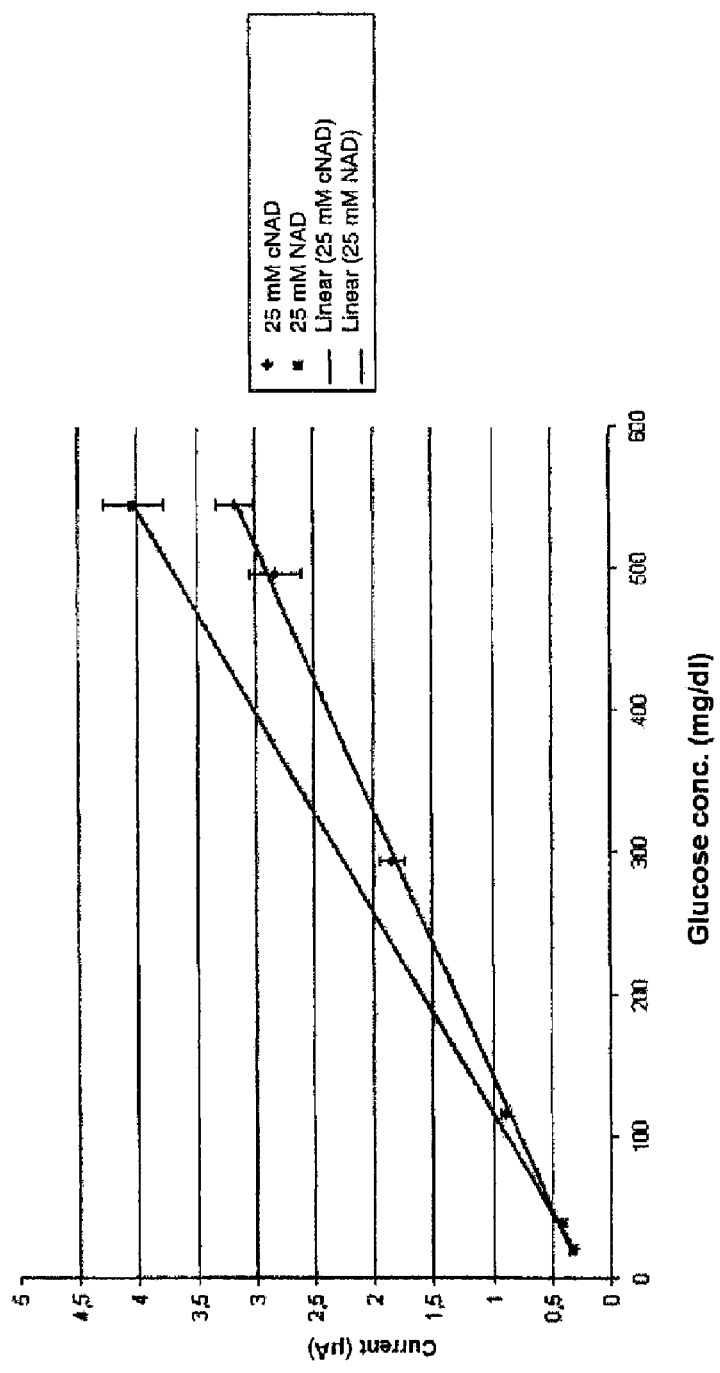
FIG. 20 is a depiction of the current measured as a function of the glucose concentration in the electrochemical determination of glucose using glucose dehydrogenase in the presence of NAD and cNAD, respectively. Test conditions: 25 mM NAD and cNAD, respectively; 2.5 seconds delay; 5 seconds measurement time.

As alternative to photometry it is also possible to employ an electrochemical measurement for the purpose of determining analytes. Thus, the current required to reoxidize the reduced mediator was found to be linearly dependent on the glucose concentration (FIG. 20) both with a test element which, besides glucose dehydrogenase, comprised NAD as coenzyme and 1-(3-carboxypropoxy)-5-ethylphenazinium trifluoromethanesulfonate as mediator, and with a corresponding system which included the stabilized coenzyme cNAD instead of NAD.

It has thus been shown that determination of analytes using the dehydrogenase/stable coenzyme system is also possible by means of electrochemical detection and evaluation with another wavelength which is independent of the coenzyme. The overall formulation ought also to be further stabilized through the use of the stable enzyme/coenzyme pair.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

We claim:

1. A storage composition comprising a dehydrogenase and a stable artificial coenzyme in direct contact with each other wherein the dehydrogenase is stable upon storage for at least two weeks at a temperature of at least 20° C. wherein the dehydrogenase retains 50% of its initial enzymatic activity when in the presence of the stable artificial coenzyme, wherein the dehydrogenase is selected from a glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase and L-amino-acid dehydrogenase (E.C.1.4.1.5), and wherein the stable artificial coenzyme is selected from compounds having a general formula (II):

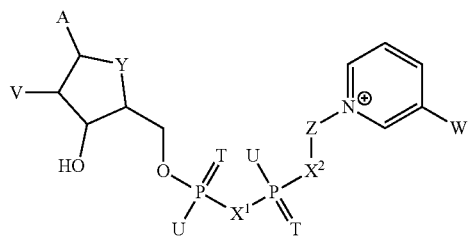

with

A=adenine or an analogue thereof, wherein the adenine analogue is C8-substituted adenine, N6-substituted adenine, 7-deaza adenine, 8-aza adenine, formycin, 7-deaza adenine with 8-aza, and 7-deaza adenine variants substituted in position 7 by halogen, C1-C6-alkynyl, -alkenyl or -alkyl, T=in each case is independently O or S, U=in each case independently OH, SH, $BH_3^-$

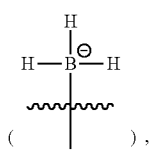

or $BCNH_2^-$

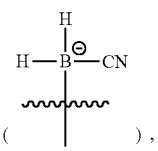

V=in each case independently OH or a phosphate group;

W=COOR, $CON(R)_2$, COR, $CSN(R)_2$ with R=in each case independently H or $C_1$-$C_2$-alkyl, $X^1$, $X^2$=in each case independently O, $CH_2$, $CHCH_3$, $C(CH_3)_2$, NH, or $NCH_3$, Y=NH, S, O, or $CH_2$, and wherein Z is a carbocyclic or heterocyclic ring of the general formula (III)

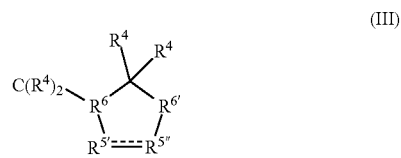

wherein the bond betweein $R^{5'}$ and $R^{5''}$ is a single or double bond, with $R^4$ =in each case independently H, F, Cl, or $CH_3$, where $R^{5'}$=O, S, NH, $NC_1$-$C_2$-alkyl, $CR^4_2$, CHOH, or $CHOCH_3$, and $R^{5'}$=$CR^4_2$, CHOH, $CHOCH_3$ if there is a single bond between $R^{5'}$ and $R^{5''}$, where $R^{5'}$=$R^{5''}$=$CR^4$ if there is a double bond between $R^{5'}$ and $R^{5''}$, and $R^6$, $R^{6'}$=in each case independently CH or $CCH_3$, wherein the $C(R^4)_2$ is linked to $X_2$ and $R_{6'}$ is linked to the pyridine ring.

2. The storage composition of claim 1, characterized in that it has upon storage for at least four weeks at a temperature of at least 25° C., with high humidity and without a drying reagent, a decline in the enzymatic activity of less than 30% compared with the initial value.

3. The storage composition of claim 1 characterized in that it has upon storage for at least eight weeks at a temperature of at least 30° C. with high humidity and without a drying reagent, a decline in the enzymatic activity of less than 20% compared with the initial value.

4. The storage composition according to claim 1, wherein the dehydrogenase is glucose dehydrogenase.

5. The storage composition according to claim 1, characterized in that the stable artificial coenzyme is selected from stable nicotinamide adenine dinucleotide (NAD/NADH)- and nicotinamide adenine dinucleotide phosphate (NADP/NADPH) derivatives.

6. The storage composition according to claim 1, characterized in that the stable coenzyme is selected from compounds having the general formula (II) wherein W=$CONH_2$ or $COCH_3$.

7. The storage composition according to claim 1, wherein in Formula III $R^5$ is $CH_2$.

8. The storage composition according to claim 1, wherein in Formula III $R^{5'}$ is selected from $CH_2$, CHOH and NH.

9. The storage composition according to claim 1, wherein in Formula III $R^{5'}$ and $R^{5''}$ are each CHOH.

10. The storage composition according to claim 1, wherein in Formula III $R^{5'}$ is NH and $R^{5'}$ is $CH_2$.

11. The storage composition according to claim 1, characterized in that the stable coenzyme is carbaNAD.

12. The storage composition according to claim 1, characterized in that the dehydrogenase is a mutated glucose dehydrogenase including at least one mutation at one of positions 96, 170 and 252 of the amino acid sequence of the wildtype glucose dehydrogenase of Bacillus subtilis.

13. The storage composition according to claim 12, wherein the mutated glucose dehydrogenase comprises the amino acid sequence as shown in SEQ ID NO. 1 or SEQ ID NO. 2.

14. A detection reagent for determining an analyte which detection reagent contains the storage composition according to claim 1.

15. A test element characterized in that it contains the storage composition according to claim 1.

16. A test element characterized in that it contains a detection reagent according to claim 14.

17. The storage composition of claim 1, characterized in that the dehydrogenase is a mutated glucose dehydrogenase.

18. The storage composition of claim 1, characterized in that the dehydrogenase is a mutated glucose dehydrogenase with increased thermal or hydrolytic stability compared to the respective wild type glucose dehydrogenase.

19. The storage composition of claim 1, wherein the storage composition does not contain a drying agent.

20. The storage composition of claim 1, wherein the storage composition is a dry composition.

* * * * *

SEQUENCE LISTING

<160> NUMBER OF SEQ ID NOS: 2

<210> SEQ ID NO 1

```
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant of glucose dehydrogenase from Bacillus
      subtilis
<220> FEATURE:
<221> NAME/KEY: MUTAGEN
<222> LOCATION: (96)..(96)
<220> FEATURE:
<221> NAME/KEY: MUTAGEN
<222> LOCATION: (170)..(170)

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Gly
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260

<210> SEQ ID NO 2
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant of glucose dehydrogenase from Bacillus
```

```
       subtilis
<220> FEATURE:
<221> NAME/KEY: MUTAGEN
<222> LOCATION: (170)..(170)
<220> FEATURE:
<221> NAME/KEY: MUTAGEN
<222> LOCATION: (252)..(252)

<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Val Ala Val Trp Leu Ala Ser Lys Glu Ser Ser Tyr Val Thr Gly
225                 230                 235                 240

Ile Thr Leu Phe Ala Asp Gly Gly Met Thr Leu Tyr Pro Ser Phe Gln
                245                 250                 255

Ala Gly Arg Gly
            260
```